(12) United States Patent
Filiberti et al.

(10) Patent No.: US 10,500,418 B2
(45) Date of Patent: Dec. 10, 2019

(54) SYSTEM AND METHOD FOR PATIENT-SPECIFIC MOTION MANAGEMENT FOR TREATMENT

(71) Applicant: Varian Medical Systems International AG, Cham (CH)

(72) Inventors: Reto W. Filiberti, Steinhausen (CH); Stefan G. Scheib, Wadenswil (CH); Michael Huber, Beinwil am See (CH)

(73) Assignee: Varian Medical Systems International AG, Cham (CH)

( * ) Notice: Subject to any disclaimer, the term of this patent is extended or adjusted under 35 U.S.C. 154(b) by 31 days.

(21) Appl. No.: 15/398,683

(22) Filed: Jan. 4, 2017

(65) Prior Publication Data

US 2018/0185671 A1 Jul. 5, 2018

(51) Int. Cl.
*A61N 5/10* (2006.01)
*A61B 90/00* (2016.01)
*A61B 5/113* (2006.01)

(52) U.S. Cl.
CPC ............ *A61N 5/1049* (2013.01); *A61B 5/113* (2013.01); *A61B 5/1135* (2013.01); *A61B 90/39* (2016.02); *A61N 5/1065* (2013.01); *A61N 5/1068* (2013.01); *A61N 5/1069* (2013.01); *A61N 5/1081* (2013.01); *A61B 2090/3937* (2016.02); *A61N 2005/1052* (2013.01); *A61N 2005/1055* (2013.01); *A61N 2005/1058* (2013.01); *A61N 2005/1059* (2013.01); *A61N 2005/1061* (2013.01)

(58) Field of Classification Search
CPC ............ A61B 2090/3937; A61B 5/113; A61B 5/1135; A61B 90/39; A61N 5/1049; A61N 5/1065; A61N 5/1068; A61N 5/1069; A61N 5/1081
See application file for complete search history.

(56) References Cited

U.S. PATENT DOCUMENTS

| 2009/0052623 | A1 | 2/2009 | Tome et al. |
| 2010/0172469 | A1 | 7/2010 | Poulsen et al. |
| 2012/0041773 | A1 | 2/2012 | Kunz |
| 2013/0109904 | A1 | 5/2013 | Siljamaki et al. |

(Continued)

OTHER PUBLICATIONS

Written Opinion dated Dec. 3, 2018 for corresponding PCT Application No. PCT/EP2018/050131, 6 pages.

(Continued)

*Primary Examiner* — Siamak Harandi
(74) *Attorney, Agent, or Firm* — Vista IP Law Group, LLP

(57) ABSTRACT

An apparatus for assisting a selection of motion management technique for use with a treatment machine having an energy source, comprises: one or more input for obtaining motion trace of a target to be treated, and/or for obtaining motion data of a fiducial; and a motion management processor configured to determine motion management data based at least in part on at least a portion of the motion trace of the target and/or at least a portion of the motion data of the fiducial, wherein the motion management data indicates desirability and/or undesirability of one or more motion management option(s); wherein the motion management processor is also configured to output the motion management data for assisting the selection of the motion management technique for use with the treatment machine.

69 Claims, 19 Drawing Sheets

(56) References Cited

U.S. PATENT DOCUMENTS

2013/0131426 A1    5/2013  Sumanaweera et al.
2015/0045604 A1*  2/2015  Sawkey ............... A61N 5/1068
                                                       600/1
2016/0232668 A1*  8/2016  Ishiraha ................ A61B 6/032

OTHER PUBLICATIONS

International Search Report and Written Opinion dated Apr. 17, 2018 for corresponding PCT Application No. PCT/EP2018/050131, 14 pages.

* cited by examiner

| Internal surrogate | | | | | | | | |
|---|---|---|---|---|---|---|---|---|
| Motion management | Evaluation criteria | | | | | | | |
| | Target motion >5mm | Surrogate motion >5mm | Surrogate and target move in sync | Surrogate motion visible from imaging direction | Target stays >30% at inhale | Target stays >30% at exhale | Min. distance between critical organ and target >10 mm | Min. distance between critical organ and target >20 mm |
| Motion management based on internal surrogate | Y | Y | Y | Y | | | | |
| Surrogate based breath-hold gating | Y | Y | Y | Y | | | | |
| Surrogate based gating | Y | Y | Y | Y | | | | |
| Gating or breath-hold at inhale | Y | Y | Y | Y | Y | | | |
| Gating or breath-hold at exhale | Y | Y | Y | Y | | Y | | |
| Field or couch tracking | Y | Y | Y | Y | | | Y | |
| Combined field and couch tracking possible | Y | Y | Y | Y | | | | Y |

FIG. 6A

| External marker | Evaluation criteria | | | | | | | |
|---|---|---|---|---|---|---|---|---|
| Motion management | Target motion > 5mm | Surrogate motion > 5mm | Marker and target move in sync | Marker motion visible from imaging direction | Target stays > 30% at inhale | Target stays > 30% at exhale | Min. distance between critical organ and target > 10 mm | Min. distance between critical organ and target > 20 mm |
| Motion management based on external marker | Y | Y | Y | Y | | | | |
| Marker based breath-hold gating | Y | Y | Y | Y | | | | |
| Marker based gating | Y | Y | Y | Y | | | | |
| Gating or breath-hold at inhale | Y | Y | Y | Y | Y | | | |
| Gating or breath-hold at exhale | Y | Y | Y | Y | | Y | | |
| Field or couch tracking | Y | Y | Y | Y | | | Y | |
| Combined field and couch tracking possible | Y | Y | Y | Y | | | | Y |

| Internal marker | | Evaluation criteria | | | | | |
| --- | --- | --- | --- | --- | --- | --- | --- |
| | Motion management | Target motion > 5mm | Marker motion visible from imaging direction | Target stays > 30% at inhale | Target stays > 30% at exhale | Min. distance between critical organ and target > 10 mm | Min. distance between critical organ and target > 20 mm |
| | Motion management based on implanted marker | Y | Y | | | | |
| | Internal marker based breath-hold gating | Y | Y | | | | |
| | Internal marker based gating | Y | Y | | | | |
| | Gating or breathhold at inhale | Y | Y | Y | | | |
| | Gating or breath-hold at exhale | Y | Y | | Y | | |
| | Field or couch tracking | Y | Y | | | Y | |
| | Combined field and couch tracking possible | Y | Y | | | | Y |

FIG. 6C

| Beacon Motion management | Target motion > 5mm | Target stays > 30% at inhale | Target stays > 30% at exhale | Min. distance between critical organ and target > 10 mm | Min. distance between critical organ and target > 20 mm |
|---|---|---|---|---|---|
| Motion management based on implanted beacon | Y | | | | |
| Internal beacon based breath-hold gating | Y | | | | |
| Internal beacon based gating | Y | | | | |
| Gating or breathhold at inhale | Y | Y | | | |
| Gating or breathhold at exhale | Y | | Y | | |
| Field or couch tracking | Y | | | Y | |
| Combined field and couch tracking possible | Y | | | | Y |

FIG. 6D

| Internal + external markers | | | | | | | |
|---|---|---|---|---|---|---|---|
| Motion management | Target motion > 5mm | Internal marker is visible from imaging direction | Good correlation between external and internal markers | Target stays > 30% at inhale | Target stays > 30% at exhale | Min. distance between critical organ and target > 10 mm | Min. distance between critical organ and target > 20 mm |
| Motion management based on implanted marker in combination with external marker | Y | | Y | | | | |
| Motion management based on implanted marker | Y | Y | | | | | |
| Implanted marker based breath-hold gating | Y | Y | | | | | |
| Implanted marker based gating | Y | Y | | | | | |
| Gating or breath-hold at inhale | Y | Y | Y | Y | | | |
| Gating or breath-hold at exhale | Y | Y | Y | | Y | | |
| Field or couch tracking | Y | Y | Y | | | Y | |
| Combined field and couch tracking possible | Y | Y | Y | | | | Y |

FIG. 6E

SYSTEM AND METHOD FOR PATIENT-SPECIFIC MOTION MANAGEMENT FOR TREATMENT

FIELD

An embodiment described herein relates to treatment system and method, and more specifically, to method and system for assisting selection of motion management technique for use in treatment.

BACKGROUND

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. In certain types of radiotherapy, the irradiation volume can be restricted to the size and shape of the tumor or targeted tissue region to avoid inflicting unnecessary radiation damage to healthy tissue. For example, conformal therapy is a radiotherapy technique that is often employed to optimize dose distribution by conforming the treatment volume more closely to the targeted tumor.

Normal physiological movement represents a limitation in the clinical planning and delivery of conventional radiotherapy and conformal therapy. Normal physiological movement, such as respiration or heart movement, can cause a positional movement of the tumor or tissue region undergoing irradiation. If the radiation beam has been shaped to conform the treatment volume to the exact dimensions of a tumor, then movement of that tumor during treatment could result in the radiation beam not being sufficiently sized or shaped to fully cover the targeted tumoral tissue.

One method to account for the target motion is to simply open up the field aperture to ensure that the radiation volume covers the entire extent of the tumor motion. The problem with this approach is that it irradiates an unnecessarily large volume of healthy tissue.

In another method, physiological gating of the radiation beam during treatment may be performed, with the gating signal synchronized to the movement of the tumor or of a surrogate of the tumor. Such technique may reduce the volume of healthy tissue being exposed to high dose radiation. In this approach, instruments are utilized to measure the physiological state of the patient with reference to the particular physiological movement being examined. For example, respiration has been shown to cause movements in the position of a lung tumor in a patient's body. If radiotherapy is being applied to the lung tumor, then a position sensor can be attached to the patient to measure the patient's respiration cycle. The radiation beam can be gated based upon certain threshold points within the measured respiratory cycle, such that the radiation beam is disengaged during periods in the respiration cycle that correspond to excessive movement of the lung tumor. In some cases, when gating technique is used, the beam may be gated off for a significant amount of time, thereby extending the length of the treatment session.

During treatment, target motion may result in dose intended for a lesion being delivered to normal tissue and organs at risk instead. This requires a strategic treatment decision to mitigate the effect of any anticipated motion in order to preserve the treatment intent. Many methods have been proposed or developed to reduce the dose to normal tissue, including pausing the treatment beam while the lesion is outside the beam (gating), and moving the beam to follow the lesion motion (tracking). It may be difficult, however, to compare the effectiveness of different strategies, and to determine the best strategy for a given patient. In part, this stems from the stochastic nature of the events causing the motion. Furthermore, factors contributing to the relative effectiveness, or ineffectiveness, of each treatment strategy are not always apparent prior to treatment.

SUMMARY

An apparatus for assisting a selection of motion management technique for use with a treatment machine having an energy source, comprises: one or more input for obtaining a motion trace of a target in a patient to be treated, and/or for obtaining motion data of a fiducial; and a motion management processor configured to determine motion management data based at least in part on at least a portion of the motion trace of the target and/or at least a portion of the motion data of the fiducial, wherein the motion management data indicates desirability and/or undesirability of one or more motion management option(s); wherein the motion management processor is also configured to output the motion management data for assisting the selection of the motion management technique for use with the treatment machine.

Optionally, the apparatus further includes a target motion analyzer configured to determine whether a motion of the target is more than a prescribed amount.

Optionally, the motion management data indicates that no motion management option is desirable if the motion of the target is less than the prescribed amount.

Optionally, the fiducial comprises a surrogate inside the patient.

Optionally, the apparatus further includes a surrogate motion analyzer configured to determine whether a motion of the surrogate is more than a prescribed amount, wherein the motion management data indicates that no motion management is desirable if the motion of the surrogate is less than the prescribed amount.

Optionally, the fiducial comprises a surrogate inside the patient, and the apparatus further comprises a synchronous motion detector configured to determine whether the surrogate moves synchronously with the target.

Optionally, the motion management data indicates motion management based on surrogate is undesirable if the surrogate does not move synchronously with the target.

Optionally, the fiducial comprises a marker coupled to the patient, and the apparatus further comprises a synchronous motion detector configured to determine whether the marker moves synchronously with the target.

Optionally, the motion management data indicates that motion management based on the marker is undesirable if the marker does not move synchronously with the target.

Optionally, the motion management data indicates whether the marker motion and the target motion are synchronous in phase to each other. In other embodiments, instead of marker motion and target motion, the motion management data may indicate whether other sources of motion are synchronous in phase to each other.

Optionally, the fiducial comprises a marker, and the apparatus further comprises a visibility detector configured to determine whether a motion of the marker is visible from an imaging direction; and wherein the motion management processor is configured to determine the motion management data based at least in part on whether the motion of the marker is visible from the imaging direction.

Optionally, the apparatus further includes a target motion analyzer configured to determine whether the target stays at an inhale phase for more than a prescribed duration, wherein the motion management processor is configured to determine the motion management data based at least in part on whether the target stays at the inhale phase for more than the prescribed duration.

Optionally, the motion management data indicates that gating-at-inhale and breath-hold-at-inhale are desirable motion management options if the target stays at the inhale phase for more than the prescribed duration.

Optionally, the apparatus further includes a target motion analyzer configured to determine whether the target stays at an exhale phase for more than a prescribed duration, wherein the motion management processor is configured to determine the motion management data based at least in part on whether the target stays at the exhale phase for more than the prescribed duration.

Optionally, the motion management data indicates that gating-at-exhale and breath-hold-at-exhale are desirable motion management options if the target stays at the exhale phase for more than the prescribed duration.

Optionally, the apparatus further includes a distance analyzer configured to determine whether a distance between the target and a critical organ is more than a first threshold.

Optionally, the motion management data indicates that field-tracking and/or couch-tracking is desirable motion management option(s) or not if the distance between the target and the critical organ is not more than the first threshold.

Optionally, the apparatus further includes a distance analyzer configured to determine whether the distance between the target and the critical organ is more than a second threshold that is larger than the first threshold.

Optionally, the motion management data indicates that field-tracking and/or couch-tracking is a desirable motion management option if the distance between the target and the critical organ is not more than the second threshold.

Optionally, the motion management data indicates that field-tracking in combination with couch-tracking is a desirable motion management option if the distance between the target and the critical organ is more than the second threshold.

Optionally, the apparatus further includes a display for displaying the motion management data.

Optionally, the motion trace comprises a segmentation of the target.

Optionally, the motion management processor is configured to provide the motion management data to a treatment planning module.

Optionally, the one or more input is also configured to obtain a signal input representing a change of one or more parameters involved in a treatment planning; and wherein the motion management processor is configured to perform calculation using the input to obtain new motion management data.

Optionally, the motion trace comprises a video formed by CT image data, MRI data, PET, ultrasound or x-ray image data.

Optionally, the motion data represents a real motion or a simulated motion.

Optionally, the motion trace, the motion data, or both, are data generated during a treatment session.

Optionally, the motion management processor is configured to determine the motion management data based also on data generated during the treatment session.

Optionally, the apparatus further includes dosimetry analyzer configured to determine dosimetry impact of one or more of the motion management option(s).

Optionally, the motion management processor is configured to analyze the motion trace and the motion data to determine whether a plurality of criteria is met; wherein the motion management processor is configured to determine the motion management data based on a result of the analyzing.

Optionally, the motion management processor is configured to classify a first subset of all available motion management options as desirable motion management option(s), and to classify a second subset of the available motion management options as undesirable motion management option(s) based on the result of the analyzing.

Optionally, the motion management data also indicates one or more of: an amount of movement of the target over a breathing cycle, an amount of movement of the target inside a percentage of a breathing amplitude, an amount of movement of the target over a certain phase range of a breathing cycle, gantry angle(s) or a range of gantry angles at or over which a distance between the target and a critical structure is less than a prescribed value, a duration for which the target does not shift by more than a prescribed distance during an exhale phase, a duration for which the target does not shift by more than a prescribed distance during an inhale phase, motion information regarding an organ at risk, an amount of movement of a critical organ over a breathing cycle, an amount of movement of the critical organ inside a percentage of a breathing amplitude, an amount of movement of the critical organ over a certain phase range of the breathing cycle, a duration for which the critical organ does not shift by more than a prescribed distance during the exhale phase, a duration for which the critical organ does not shift by more than a prescribed distance during the inhale phase, dose volume parameter that depends on a chosen motion management scheme, an estimated treatment time, dose robustness measure based on motion variability, or any combination of the foregoing.

Optionally, the motion management data comprises one or more setting recommendations selected from the group consisting of: gating window for performing gating of radiation deliveries, gating window at different gantry angles, a change in gating window(s) depending on angles or angle segments, tracking parameter(s) for MLC or couch, optimal collimator settings at different gantry positions, and parameter suggestion for predicting motion.

Optionally, the motion management technique corresponds with one of the one or more motion management option(s).

A processor-implemented method for assisting a selection of motion management technique for use with a treatment machine having an energy source, includes: obtaining motion trace of a target in a patient to be treated and/or motion data of a fiducial; determining, using a motion management processor, motion management data based at least in part on at least a portion of the motion trace of the target and at least a portion of the motion data of the fiducial, wherein the motion management data indicates desirability and/or undesirability of one or more motion management option(s); and outputting the motion management data for assisting the selection of the motion management technique for use with the treatment machine.

Optionally, the method further includes determining whether a motion of the target is more than a prescribed amount.

Optionally, the motion management data indicates that no motion management option is desirable if the motion of the target is less than the prescribed amount.

Optionally, the fiducial comprises a surrogate inside the patient.

Optionally, the method further includes determining whether a motion of the surrogate is more than a prescribed amount, wherein the motion management data indicates that no motion management is desirable if the motion of the surrogate is less than the prescribed amount.

Optionally, the fiducial comprises a surrogate inside the patient, and the method further comprises determining whether the surrogate moves synchronously with the target.

Optionally, the motion management data indicates motion management based on surrogate is undesirable if the surrogate does not move synchronously with the target.

Optionally, the fiducial comprises a marker coupled to the patient, and the method further comprises determining whether the marker moves synchronously with the target.

Optionally, the motion management data indicates that motion management based on the marker is undesirable if the marker does not move synchronously with the target.

Optionally, the fiducial comprises a marker, and the method further comprises determining whether a motion of the marker is visible from an imaging direction; and wherein the motion management data is determined based at least in part on whether the motion of the marker is visible from the imaging direction.

Optionally, the method further includes determining whether the target stays at an inhale phase for more than a prescribed duration, wherein the motion management data is determined based at least in part on whether the target stays at the inhale phase for more than the prescribed duration.

Optionally, the motion management data indicates that gating-at-inhale and breath-hold-at-inhale are desirable motion management options if the target stays at the inhale phase for more than the prescribed duration.

Optionally, the method further includes determining whether the target stays at an exhale phase for more than a prescribed duration, wherein the motion management data is determined based at least in part on whether the target stays at the exhale phase for more than the prescribed duration.

Optionally, the motion management data indicates that gating-at-exhale and breath-hold-at-exhale are desirable motion management options if the target stays at the exhale phase for more than the prescribed duration.

Optionally, the method further includes determining whether a distance between the target and a critical organ is more than a first threshold.

Optionally, the motion management data indicates that field-tracking and/or couch-tracking is desirable motion management option(s) or not if the distance between the target and the critical organ is not more than the first threshold.

Optionally, the method further includes determining whether the distance between the target and the critical organ is more than a second threshold that is larger than the first threshold.

Optionally, the motion management data indicates that field-tracking and/or couch-tracking is a desirable motion management option if the distance between the target and the critical organ is not more than the second threshold.

Optionally, the motion management data indicates that field-tracking in combination with couch-tracking is a desirable motion management option if the distance between the target and the critical organ is more than the second threshold.

Optionally, the method further includes displaying the motion management data.

Optionally, the motion trace comprises a segmentation of the target.

Optionally, the method further includes providing the motion management data, by a motion management module, to a treatment planning module.

Optionally, the method further includes: obtaining input representing a change of one or more parameters involved in a treatment planning; and performing calculation using the input to obtain new motion management data.

Optionally, the act of obtaining input and the act of performing calculation using the input are repeated.

Optionally, the motion trace comprises a video formed by CT image data, MRI data, PET, ultrasound or x-ray image data.

Optionally, the motion data represents a real motion or a simulated motion.

Optionally, the motion trace, the motion data, or both, are data generated during a treatment session.

Optionally, the method further includes obtaining data generated during a treatment session, wherein the motion management data is determined based also on the data generated during the treatment session.

Optionally, the method further includes determining dosimetry impact of one or more of the motion management option(s).

Optionally, the method further includes analyzing the motion trace and the motion data to determine whether a plurality of criteria is met; wherein the motion management data is determined based on a result of the analyzing.

Optionally, the method further includes classifying a first subset of all available motion management options as desirable motion management option(s), and classifying a second subset of the available motion management options as undesirable motion management option(s) based on the result of the analyzing.

Optionally, the motion management data also indicates one or more of: an amount of movement of the target over a breathing cycle, an amount of movement of the target inside a percentage of a breathing amplitude, an amount of movement of the target over a certain phase range of a breathing cycle, gantry angle(s) or a range of gantry angles at or over which a distance between the target and a critical structure is less than a prescribed value, a duration for which the target does not shift by more than a prescribed distance during an exhale phase, a duration for which the target does not shift by more than a prescribed distance during an inhale phase, motion information regarding an organ at risk, an amount of movement of a critical organ over a breathing cycle, an amount of movement of the critical organ inside a percentage of a breathing amplitude, an amount of movement of the critical organ over a certain phase range of the breathing cycle, a duration for which the critical organ does not shift by more than a prescribed distance during the exhale phase, a duration for which the critical organ does not shift by more than a prescribed distance during the inhale phase, dose volume parameter that depends on a chosen motion management scheme, an estimated treatment time, dose robustness measure based on motion variability, or any combination of the foregoing.

Optionally, the motion management data comprises one or more setting recommendations selected from the group consisting of: gating window for performing gating of radiation deliveries, gating window at different gantry angles, a change in gating window(s) depending on angles or angle segments, tracking parameter(s) for MLC or couch, optimal collimator settings at different gantry positions, and parameter suggestion for predicting motion.

Optionally, the motion management technique corresponds with one of the one or more motion management option(s).

Other and further aspects and features will be evident from reading the following detailed description.

BRIEF DESCRIPTION OF THE DRAWINGS

The drawings illustrate the design and utility of various features described herein, in which similar elements are referred to by common reference numerals. These drawings are not necessarily drawn to scale. In order to better appreciate how the above-recited and other advantages and objects are obtained, a more particular description will be rendered, which are illustrated in the accompanying drawings. These drawings depict only exemplary features and are not therefore to be considered limiting in the scope of the claims.

FIGS. 6A-6E illustrate examples of data structures for use by the apparatus of FIG. 4 and/or the method of FIG. 5.

DETAILED DESCRIPTION

Figure 1A:
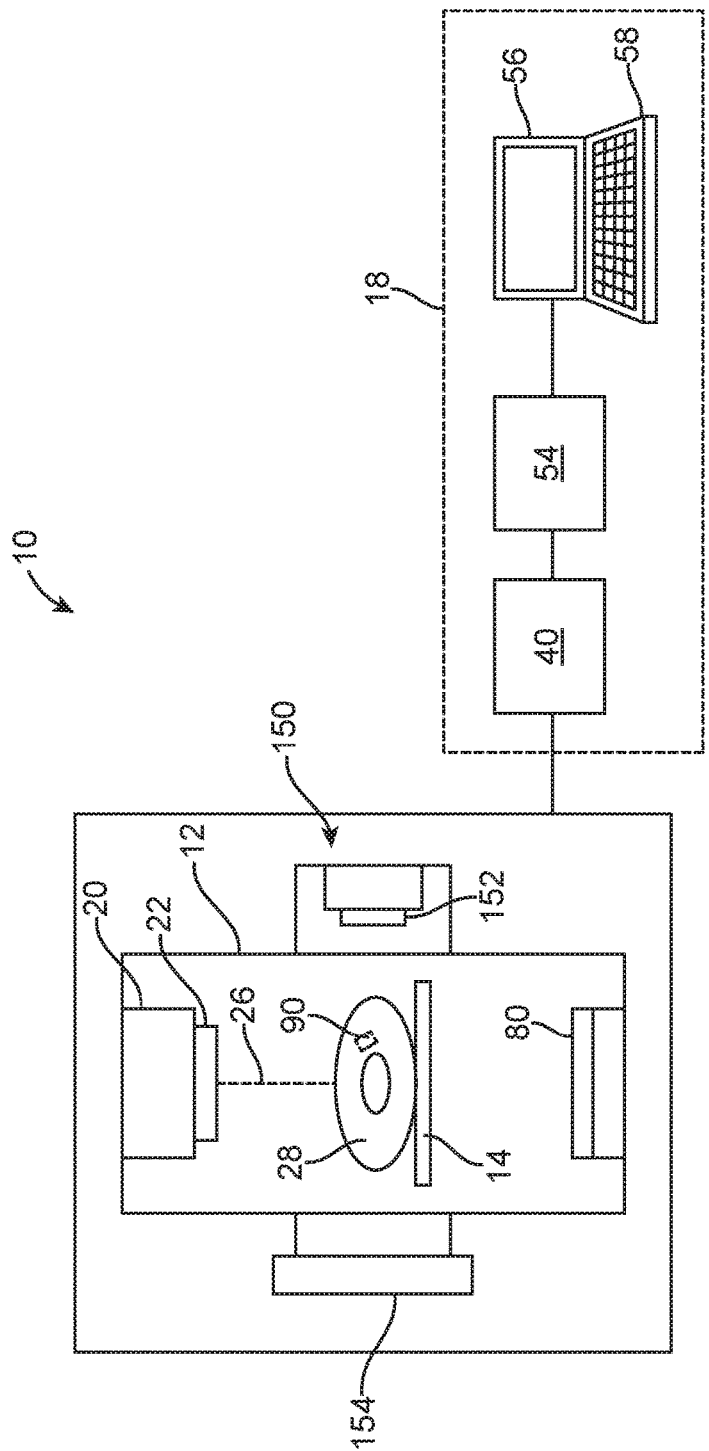
FIGS. 1A-1E illustrate medical systems with different respective position monitoring systems for motion management during treatment.

Various features are described hereinafter with reference to the figures. It should be noted that the figures are not drawn to scale and that the elements of similar structures or functions are represented by like reference numerals throughout the figures. It should be noted that the figures are only intended to facilitate the description of the features. They are not intended as an exhaustive description of the claimed invention or as a limitation on the scope of the claimed invention. In addition, an illustrated feature needs not have all the aspects or advantages shown. An aspect or an advantage described in conjunction with a particular feature is not necessarily limited to that feature and can be practiced in any other features even if not so illustrated, or if not so explicitly described.

FIG. 1A illustrates a radiation system 10. The system 10 is a treatment system that includes a gantry 12, a patient support 14 for supporting a patient 28, and a control system 18 for controlling an operation of the gantry 12. The gantry 12 is in a form of an arm, but in other embodiments, the gantry 12 may have other forms (such as a ring form, etc.). The system 10 also includes a radiation source 20 that projects a beam 26 of radiation towards a patient 28 while the patient 28 is supported on support 14, and a collimator system 22 for controlling a delivery of the radiation beam 26. The collimator may be configured to adjust a cross sectional shape of the beam 26. The radiation source 20 can be configured to generate a cone beam, a fan beam, or other types of radiation beams in different embodiments.

As shown in the figure, the system 10 also includes an imager 80, located at an operative position relative to the source 20 (e.g., under the support 14). In the illustrated embodiments, the radiation source 20 is a treatment radiation source for providing treatment energy. In such cases, the treatment energy may be used to obtain images. In order to obtain imaging using treatment energies, the imager 80 is configured to generate images in response to radiation having treatment energies (e.g., MV imager). In other embodiments, in addition to being a treatment radiation source, the radiation source 20 can also be a diagnostic radiation source for providing diagnostic energy for imaging purpose. In further embodiments, the system may include the radiation source 20 for providing treatment energy, and one or more other radiation sources for providing diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. In other embodiments, the radiation source 20 may be configured to generate radiation at other energy ranges.

In the illustrated embodiments, the control system 18 includes a processing unit 54, such as a computer processor, coupled to a control 40. The control system 18 may also include a monitor 56 for displaying data and an input device 58, such as a keyboard or a mouse, for inputting data. The operation of the radiation source 20 and the gantry 12 are controlled by the control 40, which provides power and timing signals to the radiation source 20, and controls a rotational speed and position of the gantry 12, based on signals received from the processor 54. In some cases, the control 40 may also control the collimator system 22 and the position of the patient support 14. Although the control 40 is shown as a separate component from the gantry 12 and the processor 54, in alternative embodiments, the control 40 can be a part of the gantry 12 or the processing unit 54.

In the illustrated embodiments, the system 10 also includes an imaging device 150 having an imaging source 150 and an imager 154. The imaging device 150 is configured to obtain one or more images of an internal part of the patient 28. The image(s) obtained by the imaging device 150 may be used to monitor a position of the patient 28. In some cases, the imaging device 150 may be configured to obtain images of an internal fiducial 90 of the patient 28. The internal fiducial 90 may be an internal structure inside the patient 28. In some embodiments, the internal structure may move in correspondence (e.g., in sync) with a target of the patient 28 that is desired to be treated. In such cases, the internal structure may be used as a surrogate for determining a position and/or movement of the target during treatment of the patient 28, and motion management based on the surrogate may be employed in some cases. Thus, the internal fiducial 90 may be imaged by the imaging device 150 (or radiation source 20 and imager 80) that functions as a position monitoring system during a treatment of the patient 28. By means of non-limiting examples, the internal fiducial 90 may be an anatomical surrogate, such as bony structure, a vessel, a natural calcification, or any other items in a body.

In some embodiments, the imaging device 150 may be a x-ray device. In such cases, the imaging source 150 comprises a radiation source. In other embodiments, the imaging device 150 may have other configurations, and may be configured to generate images using other imaging techniques. For example, in other embodiments, the imaging device 150 may be an ultrasound imaging device, a MRI device, a tomosynthesis imaging device, or any of other types of imaging devices. Also, in the above embodiments, the imaging device 150 is illustrated as being integrated with the treatment machine. In other embodiments, the imaging device 150 may be a separate device that is separate from the treatment machine. In addition, in some embodiments, the imaging device 150 may be a room-based imaging system or a couch based imaging system. In either case, the imaging device 150 may provide any form of imaging, such as x-ray imaging, ultrasound imaging, MRI, etc. Furthermore, in other embodiments, the imaging device 150 may provide in-line imaging in the sense that it may be configured to acquire images along the same direction as the treatment beam. For example, a dual-energy source may be provided to provide imaging energy for generating an image, and to provide treatment energy to treat a patient along the same direction. In still further embodiments, the imaging device 150 may be configured to provide dual energy imaging and any form of energy-resolved imaging to increase contrast in x-ray images. For example, a first part of an image may be generated using a first energy, and a second part (e.g., a more relevant part that includes a target) of the same image may be generated using a second energy that is higher than the first energy. As a result, the second part of the image will have higher contrast compared to the first part. However, the overall dose involved in generating the whole image may be reduced compared to the situation in which the entire image is generated using the second energy.

Figure 1B:
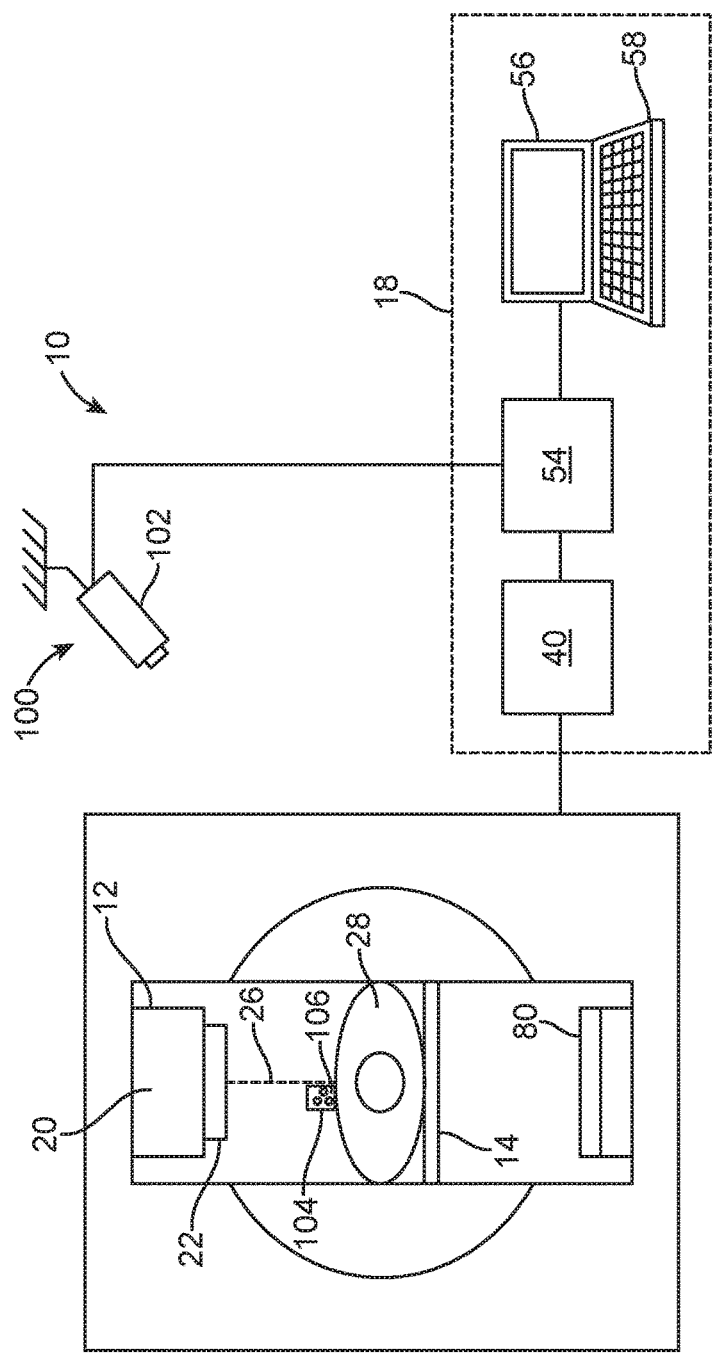

In other embodiments, instead of using an internal fiducial that is an internal part of the patient 28, the system 10 may include an external fiducial, such as a marker system, for monitoring a position of the patient 28 during treatment. FIG. 1B illustrates another system 10 that is similar to that described with reference to FIG. 1A, except that the system 10 of FIG. 1B further includes a patient position monitoring system 100 that comprises a camera 102 and a marker block 104. The marker block 104 includes a plurality of markers 106, and is configured for coupling to the patient 28 during use. For example, the marker block 104 may be placed on a patient's chest, so that the marker block 104 will move correspondingly with the patient's breathing. The camera 102 is configured to view the marker block 104, and capture images of the marker block 104. The images of the marker block 104 may be processed by the processing unit 54 to determine a position of the marker block 104. The position of the marker block 104 may, in turn, be used by the processing unit 54 to determine a breathing amplitude and/or breathing phase of the patient 28.

Alternatively, instead of capturing images of the marker block 104, the camera 102 may capture the body surface of the patient and the processing unit 54 may determine a breathing amplitude and/or phase based on image of the body surface. In one implementation, a surface scanning device (e.g., a depth sensing camera) may be configured to detect a patient's surface. A processing unit may receive the depth image, and may extract a breathing signal (e.g., a breathing phase) based on the depth image. Also, in some embodiments, the processing unit may use the surface of the patient to establish a correlation between an internal target motion and external surface motion.

Figure 2:
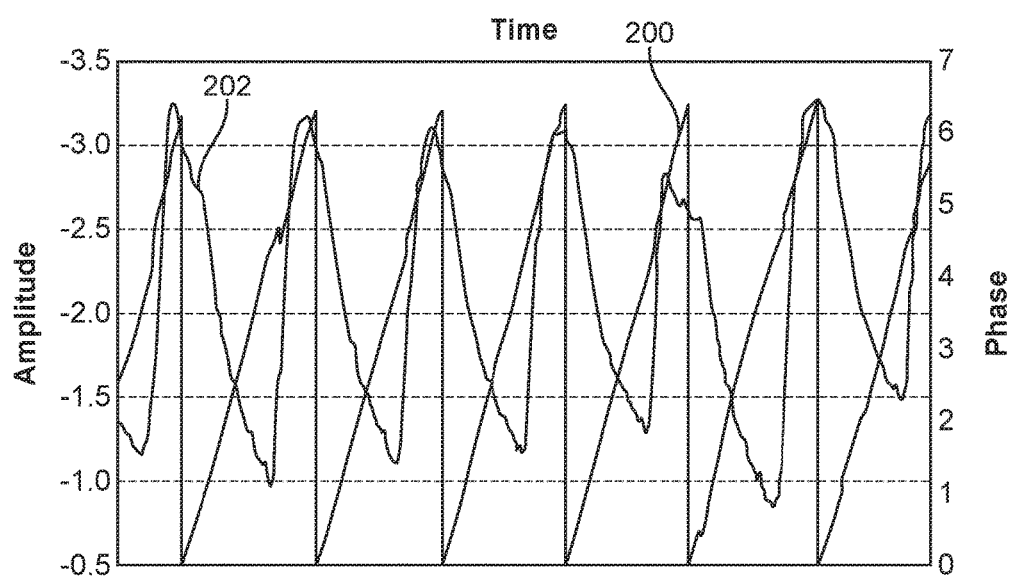
FIG. 2 illustrates an example of a phase diagram together with a breathing waveform.

In one implementation, for each breathing amplitude (which may be a position of any bodily part that moves due to breathing, a position of an object coupled to such bodily part, or any signal that is associated with breathing), the processing unit 54 determines a corresponding breathing phase for the breathing amplitude. The phase of a physiological cycle represents a degree of completeness of a physiological cycle. In some embodiments, the phases of a respiratory cycle may be represented by a phase variable having values between 0° and 360°. FIG. 2 illustrates an example of a phase diagram 200 that is aligned with a corresponding amplitude/position diagram 202. Amplitude diagram 202 includes positional points of the marker block 104 or body surface determined using embodiments of the technique described herein. Each point in the amplitude diagram 202 represents a position of the marker block 104 or a bodily part at a certain point in time. In the illustrated example, a phase value of 0° (and 360°) represents a peak of an inhale state, and the phase value varies linearly between 0° and 360° in a physiological cycle. As shown in the diagram, for each point in the amplitude diagram 202 at certain point in time, a corresponding phase value at the same point in time may be obtained. Thus, for each breathing amplitude, the processing unit 54 can determine the corresponding phase of the respiratory cycle. In some embodiments, the determined phase may be considered an example of a breathing signal.

In some embodiments, when using the system 10 of FIG. 1B, the radiation source 20 is rotated about the patient 28 to deliver treatment radiation from a plurality of gantry angles, for example, as in arc therapy. As treatment radiation is being delivered to the patient 28, the state of the patient 28, such as the patient's breathing states, may be monitored. In some embodiments, the processing unit 54 processes the signals from the camera 102 to determine breathing amplitudes of the patient 28, and then gates the delivery of the treatment radiation based on the amplitudes. For example, the processing unit 54 may cause the radiation source 20 to deliver radiation, or to stop a delivery of radiation, when the determined amplitude is within a prescribed amplitude range. In other embodiments, the processing unit 54 processes the signals from the camera 102 to determine respiratory phases of the patient 28, and then gates the delivery of the treatment radiation based on the respiratory phases. For example, the processing unit 54 may cause the radiation source 20 to deliver radiation, or to stop a delivery of radiation, when the determined phase is within a prescribed phase range. In further embodiments, the processing unit 54 processes the signals from the camera 102 to detect non-periodicity, and then gates the delivery of the treatment radiation based on the detection of non-periodicity. In other embodiments, instead of, or in addition to, controlling the delivery of radiation, the processing unit 54 may be configured to control the gantry 12 (e.g., stop, accelerate, or decelerate the gantry 12), and/or to position the patient support 14, based on the determined amplitude and/or phase, or detection of non-periodicity. In further embodiments, the processing unit 54 may be configured to control the gantry 12 and/or the radiation source 20 to track a movement of a target so that the treatment beam will follow the movement of the target.

During the treatment process, the processing unit 54 monitors the patient's 28 breathing, and correlates feature(s) of the breathing (such as breathing signals, breathing amplitudes, breathing phases, breathing hysteresis, etc.) with positions of internal target region that is being irradiated by the radiation beam 26. For example, based on images received from the camera 102, the processing unit 54 then determines the phase/amplitude of the breathing cycle. The phase of the breathing cycle or the amplitude is then used by the processing unit 54 to determine a position of the internal target region based on a pre-established relationship between breathing phase/amplitude and position of internal target region. In some embodiments, the relationship between the breathing phase/amplitude and target position may be pre-determined by a physician during a treatment planning process. For example, during a treatment planning process, it may be determined that when a patient is at breathing phase=40°, the corresponding position of the internal target region is at position X=45 mm, Y=23 mm, and Z=6 mm relative to the isocenter. This technique allows the treatment radiation system 10 to target delivery of radiation towards the target region based on breathing signals obtained by the system 10.

Figure 1C:
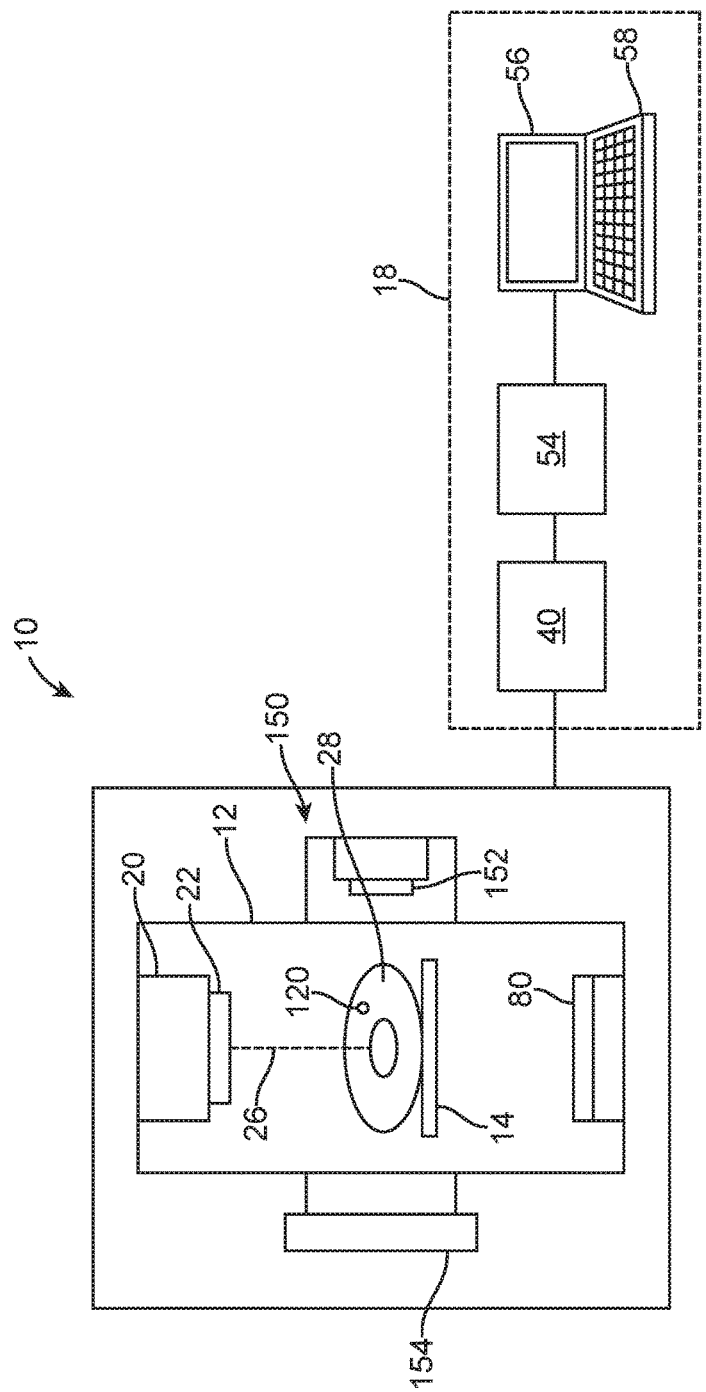

In the above embodiment of FIG. 1B, the system 10 has been described as having a camera for viewing markers on a marker block to obtain motion data representing a motion of the patient 28. Alternative, reflective markers may be placed directly on the patient's surface (e.g., on the patient's skin or the patient's garment). In other embodiments, other techniques and devices may be employed to obtain motion data representing a motion of the patient 28. For example, as shown in FIG. 1C, in other embodiments, one or more internal marker(s) 120 may be implanted inside the patient 28. During use, the imaging device 150 may image the marker(s) 120 to generate a sequence of images. The images form a video that captures a movement of the marker(s) 120. The marker(s) movement may correspond with a movement of a target that is desired to be treated. In such cases, the marker(s) 120 may be used as surrogate for viewing by the imaging device 150, which functions as position monitoring device for monitoring patient movement during treatment of the patient 28. Accordingly, the marker(s) 120 may function as a substitute/proxy for determining a position and/or motion of the target during treatment of the patient 28, and motion management based on the marker(s) 120 may be employed in some cases. In some embodiments, the marker(s) 120 may be implanted at the same organ that includes the target. In other embodiments, the marker(s) 120 may be implanted at the target. In further embodiments, the marker(s) may be implanted away from the target.

Figure 1D:
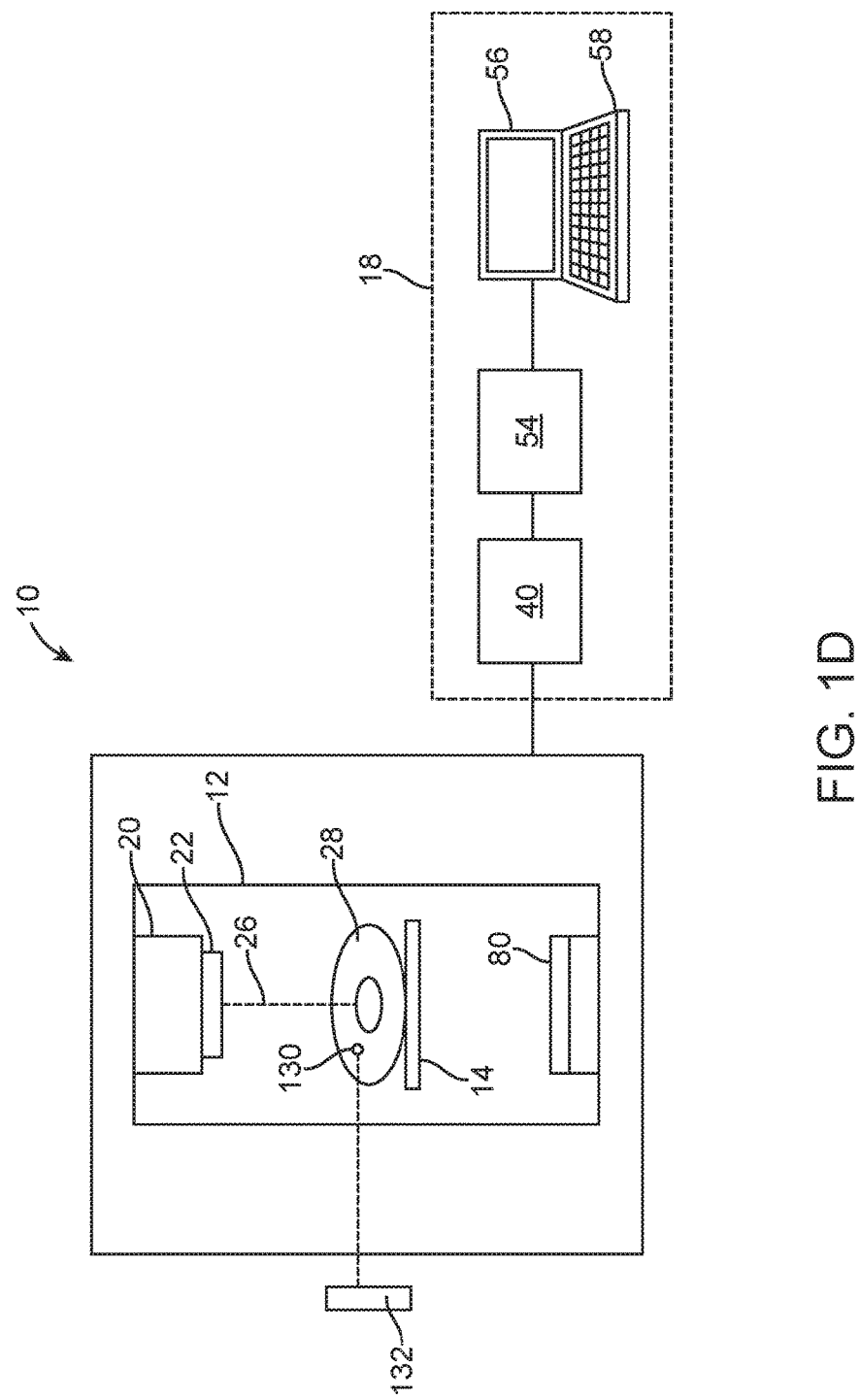

In further embodiments, the system 10 may employ internal target tracking that uses beacon(s) 130 implanted in or near the target region (e.g., tumor) along with one or more localizers 132 (FIG. 1D). In one implementation, the beacon(s) may be radio frequency or electromagnetic active or passive transponder(s). In such cases, the localizer(s) 132 may be an external array antenna. During use, the transponder(s) is localized by the external array antenna transmitting query signals and processing the transponder response signals. In other cases, the beacon may be an active beacon configured to emit a signal for sensing by the localizer(s) 132. In such cases, the localizer(s) 132 may be sensor(s) configured to sense the beacon signal. The sensed signal may then be processed by a processing unit to determine a position of the beacon 130 based on triangular methods. Accordingly, the beacon(s) 130 may function as a substitute/proxy for determining a position and/or motion of the target during treatment of the patient 28, and motion management based on the beacon(s) 130 may be employed in some cases.

Figure 1E:
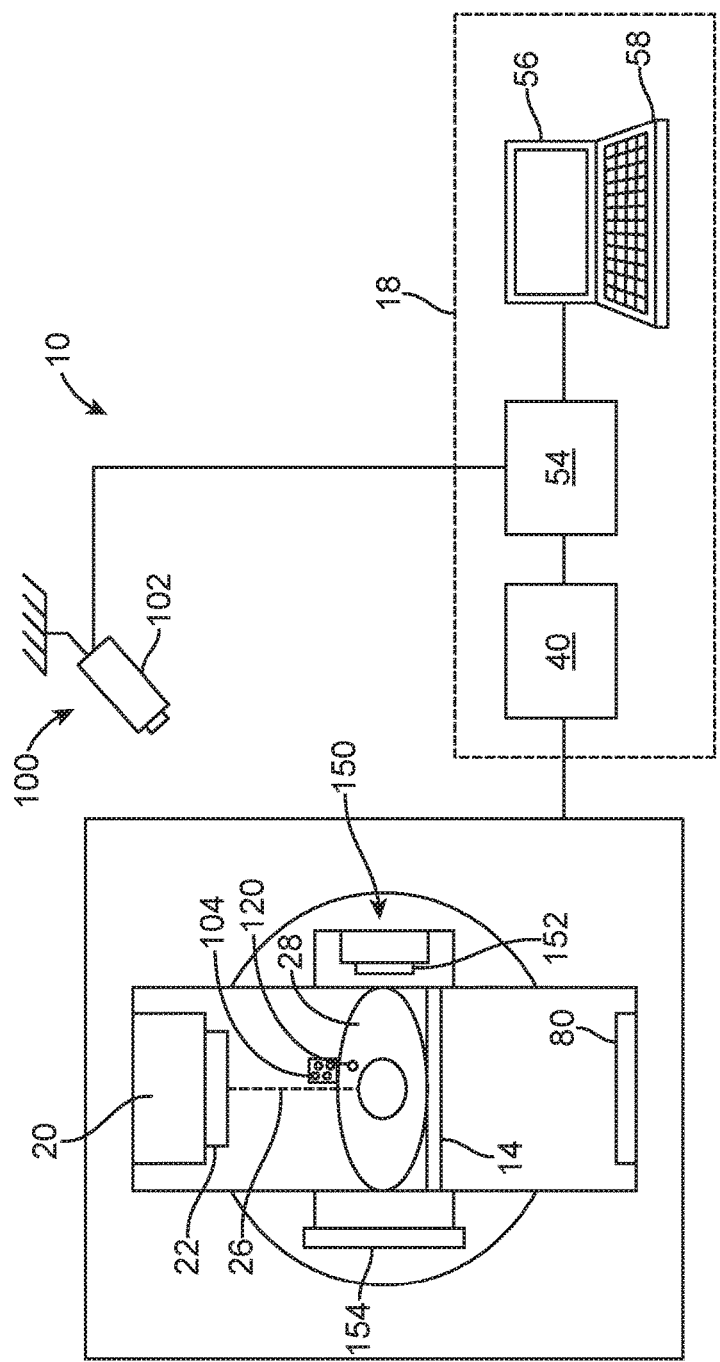

In other embodiments, the system 10 may utilize both external marker(s) and internal marker(s) for monitoring position and/or motion of the patient 28. For example, as shown in FIG. 1E, the system 10 may include the patient position monitoring system 100 (having the camera 102 for viewing the marker block 104), as well as the imaging device 100 view imaging internal marker(s) 120. In other embodiments, other object(s) may be used as external marker(s), and internal marker(s). For example, in other embodiments, an anatomical surrogate inside the patient may be used as an internal marker. Also, in other embodiments, instead of using the camera 102 to detect marker block 104, a surface scanning system may be provided to detect a surface of a patient. In such cases, the surface or a feature of the detected surface may function as external marker(s). In a system in which both external and internal markers are detected, the system may be configured to determine a correlation model that correlates motion of the external marker(s) with motion of the internal marker(s).

In other embodiments, the system 10 may include other types of devices for providing breathing information or positional information regarding a portion of the patient 28. For example, in other embodiments, the system 10 may include a strain-gauge that is coupled to the patient 28. In such cases, the strain-gauge is communicatively coupled to the processing unit 54 for providing signals that represent breathing amplitudes of the patient 28. In other embodiments, the system 10 may include a sensor coupled to the patient's mouth and/or nose for sensing the breathing of the patient. The processing unit 54 is communicatively coupled to the sensor, and receives signals from the sensor. The signals may represent the breathing amplitudes, or may be used to obtain breathing amplitudes and/or breathing phases.

In accordance with some embodiments, an apparatus and/or a method may be provided for assisting a selection of motion management technique for use with a treatment machine having an energy source. The apparatus and/or the method utilizes one or more criteria for determining whether a motion management option is desirable or undesirable. In some cases, there may be different motion management options that are available. For example, the available motion management options may include managing motion based on an internal surrogate(s), managing motion based on external marker(s), managing motion based on implanted marker(s), gating at a breathing phase (e.g., inhale, exhale, etc.), breath-hold at a breathing phase (e.g., inhale, exhale, etc.), field tracking, couch tracking, combined field and couch tracking, etc. Depending on the type of patient position monitoring technique selected, and/or other criteria, one or more of the motion management options may be desirable or undesirable.

It should be noted that field tracking refers to actively shaping an energy beam with using a collimator based on target motion. The collimator may be a multi-leaves collimator (MLC). Thus, MLC tracking may be an example of field tracking.

Figure 3A:
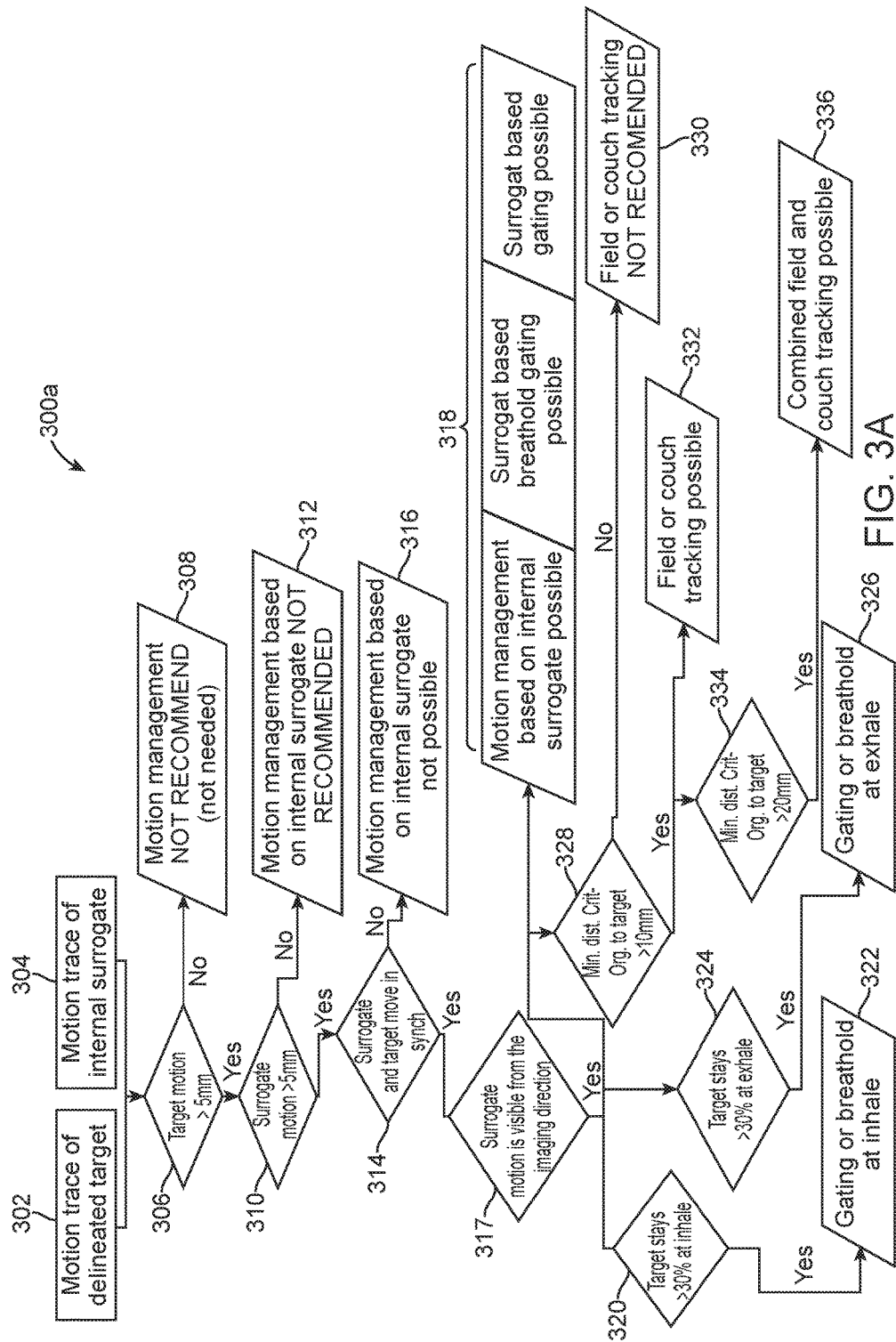
FIG. 3A illustrates an example of an algorithm.

FIG. 3A illustrates an example of an algorithm 300a that may be employed for providing motion management data that indicates a desirability and/or undesirability of one or more motion management option(s). The algorithm 300a of FIG. 3A is for determining whether one or more of the available motion management options are desirable for managing motion based on an internal surrogate (a surrogate that is inside the patient). An example of a medical system that utilizes internal surrogate for motion management is illustrated in FIG. 1A. The surrogate may be an anatomical structure in the patient that is different from the target, or it may be any other object (e.g., one or more markers) that is different from the target.

First, motion trace of a target is obtained (item 302), and/or motion data of a surrogate of the target is obtained (item 304). The target may be any part of the patient to be treated, and so the target may be a tumor for example, or tissue (in the patient to be treated) that is next to or away from the tumor. In some cases, the tissue may be critical tissue that is desired to be protected. The tissue may be within a field of "view" of the radiation beam, or may be outside the field of view of the radiation beam.

In some embodiments, the motion trace of the target may be a sequence of images indicating motion of the target. In other embodiments, the motion trace may be positional data representing positions of the target over time. In addition, in some cases, the motion trace of the target may be obtained by analyzing a sequence of images to determine positions of the target in the respective images in the sequence. Also, in some embodiments, motion data of the internal surrogate may be positional data of the surrogate over time representing a motion of the surrogate. In some embodiments, items 302, 304 may be performed by an apparatus with one or more input(s) that receive the motion trace of the target and the motion data of the internal surrogate.

Next, the motion trace of the target is analyzed to determine whether a motion of the target is more than a prescribed target motion threshold (e.g., 5 mm in the example) (item 306). In other embodiments, the prescribed target motion threshold may be more than 5 mm or less than 5 mm. It should be noted that the prescribed amount may be a prescribed distance (e.g., amplitude) or a prescribed phase of a motion. Thus, a motion of the target may be considered as being more than a prescribed amount if it motion amplitude exceeds a prescribed amplitude, or if its motion phase exceeds the prescribed phase.

If the motion of the target is not greater than the prescribed target motion threshold, then the algorithm 300a may determine a motion management data indicating that no motion management is desirable (item 308). In some embodiments, item 306 may be performed by a target motion analyzer, which analyzes the motion trace of the target to determine if a motion amplitude is more than the prescribed target motion threshold (e.g., using a comparator).

It should be noted that as used in this specification, the term "motion management data" may be a number, a text, a symbol, a graphical data, a statement, an audio signal, an audio indication, a signal for activating a visual indicator, etc., or any combination of the foregoing, which represents and/or indicates whether a motion management option is desirable or undesirable. Also, a motion management option that is "desirable" may be a motion management option that is possible or that is recommended. Accordingly, the term "desirable" should not be limited to motion management option that is "in favor", and may cover motion management option that is "possible" (for use to achieve a certain treatment outcome). Similarly, a motion management option that is "undesirable" may be a motion management option that is not possible, or that is not recommended.

Continuing with the above example, if the motion of the target is greater than the prescribe target motion threshold, the algorithm 300a then determines whether a motion of the surrogate is greater than a prescribed surrogate motion threshold by analyzing the motion data of the surrogate (item 310). In the example, the prescribed surrogate motion threshold is 5 mm. In other embodiments, the prescribed surrogate motion threshold may be more than 5 mm or less than 5 mm. Also, the prescribed surrogate motion threshold may be the same as, or different from, the prescribe target motion threshold. In some embodiments, item 310 may be performed by a surrogate motion analyzer, which analyzes the motion data of the surrogate to determine if a motion amplitude is more than the prescribed surrogate motion threshold (e.g., using a comparator). If the motion of the surrogate is not greater than the prescribed surrogate motion threshold, then the algorithm 300a may determine a motion management data indicating that motion management based on internal surrogate is undesirable (item 312).

If the motion of the surrogate is greater than the prescribed surrogate motion threshold, then the algorithm 300a determines whether the motion of the surrogate and the motion of the target are in synch (item 314). In some embodiments, item 314 may be performed by a synchronous motion detector, which analyzes the motion trace of the target and the motion data of the surrogate to determine if the target and the surrogate move synchronously (e.g., using a waveform comparator). In one implementation, the synchronous motion detector may include a comparator configured to analyze (e.g., compare) the target motion and the surrogate motion to determine if the two motions are in sync. The comparator may calculate a correlation value representing a degree of similarity between the two motions. In some cases, amplitude values of each of the two motions may be normalized before the two motions are compared. In some embodiments, the two motions may be considered to be in sync if the correlation value is higher than a prescribed threshold, such as 0.6, and more preferably 0.7, and even more preferably 0.8, and even more preferably 0.9. Also, in some cases, the two motions do not need to be in sync through a complete breathing cycle in order for them to be considered in sync. For example, if the two motions are in sync during at least a part of a breathing cycle, they may be considered in sync. Furthermore, in some cases, the two motions do not need to be in phase in order for them to be considered in sync. For example, in some cases, there may be a stable phase correlation between the two motions, and a corresponding model representing such correlation. In such cases, a surrogate may be used instead of the target itself.

If the surrogate and the target do not move synchronously with respect to each other, then the algorithm 300a may determine a motion management data indicating that motion management based on internal surrogate is not desirable (item 316).

On the other hand, if the surrogate and the target move synchronously with respect to each other (together with the satisfaction of the criteria that the target motion is greater than the target motion threshold, and the surrogate motion is greater than the surrogate motion threshold), then the algorithm 300a may determine whether a motion of the surrogate is visible from an imaging direction (item 317). In some embodiments, item 317 may be performed by a visibility detector that determines an angle between a plane in which the surrogate motion occurs and an imaging direction. If the angle is within a prescribed range (e.g., 90°±30°), then the algorithm 300a may determine that the surrogate motion is visible from the imaging direction. In some embodiments, the imaging direction (with respect to certain coordinate system) may be input by a user. Also, in some embodiments, the plane in which the surrogate motion occurs may be input by the user, or may be calculated automatically by the visibility detector. For example, the position of the plane relative to the certain coordinate system may be input by the user. Alternatively, if the position data of the surrogate is with respect to another coordinate system, the visibility detector may transform the position data so that it is with respect to the same coordinate system as that of the imaging direction.

If the surrogate motion is visible from the imaging direction, then the algorithm 300a may determine a motion management data indicating that several motion management options may be desirable (item 318). In the illustrated example, the algorithm 300a determines that motion management based on internal surrogate, breath-hold gating based on surrogate, and gating based on surrogate, may be desirable. Gating based on surrogate (e.g., internal surrogate) is a motion management option in which the treatment beam is turned on whenever the surrogate signal is within a defined gating window. In some cases, gating based on surrogate may be used in combination with breath-hold gating, which may increase the duty cycle as compared to the gating based on free breathing.

In the illustrated example, the algorithm 300a further goes through several analyses to determine whether additional motion management option(s) may be desirable. In particular, the algorithm 300a may analyze the target motion to determine whether the target stays at a certain breathing phase (e.g., inhale) for more than a certain prescribed duration (e.g., 30% of a breathing cycle duration) (item 320). In some embodiments, item 320 may be performed by a target motion analyzer, which analyzes the motion trace of the target to determine how long the target stays within a certain breathing phase. If so, then the algorithm 300a may determine motion management data indicating that gating or breath-hold at the corresponding breathing phase (inhale in the example) may be desirable motion management option (item 322).

The algorithm 300a may also analyze the target motion to determine whether the target stays at another breathing phase (e.g., exhale) for more than a certain prescribed duration (e.g., 30%) (item 324). In some embodiments, item 324 may be performed by a target motion analyzer, which analyzes the motion trace of the target to determine how long the target stays within a certain breathing phase. If the target stays at the breathing phase for more than the prescribed duration, then the algorithm 300a may determine motion management data indicating that gating or breath-hold at the corresponding breathing phase (exhale in the example) may be desirable motion management option (item 326).

The algorithm 300a may also analyze image data to determine whether a minimum distance between the target and a critical organ is more than a first distance threshold (item 328). In some embodiments, item 328 may be performed by a distance analyzer, which measures a distance between the target and the critical organ, and compares the measured distance against the first distance threshold. If the minimum distance between the target and the critical organ is not more than the first distance threshold, then the algorithm 300a may determine motion management data indicating that field tracking and/or couch tracking is not desirable motion management option(s) (item 330). In other embodiments, if the minimum distance between the target and the critical organ is not more than the first distance threshold, then the algorithm 300a may determine motion management data indicating that field tracking and/or couch tracking is desirable motion management option(s). Optionally, if the minimum distance between the target and the critical organ is not more than the first distance threshold, the algorithm 300a may determine motion management data indicating that active beam steering is a desirable motion management option. In active beam steering, the energy beam is actively steered based on a motion of a target.

On the other hand, if the minimum distance between the target and the critical organ is more than the first distance threshold, then the algorithm 300a may determine motion management data indicating that field tracking and/or couch tracking may be a desirable motion management option (item 332).

The algorithm 300a may further determine whether the minimum distance between the target and the critical organ is more than a second distance threshold that is higher than the first distance threshold (item 334). In some embodiments, item 334 may be performed by a distance analyzer, which measures a distance between the target and the critical organ, and compares the measured distance against the second distance threshold. If the minimum distance between the target and the critical organ is more than the second distance threshold, then the algorithm 300a may determine motion management data indicating that combining field tracking and couch tracking may be a desirable motion management option (item 336).

The above example has been described with reference to internal surrogate. In other embodiments, instead of internal surrogate, external surrogate may be used.

Figure 3B:
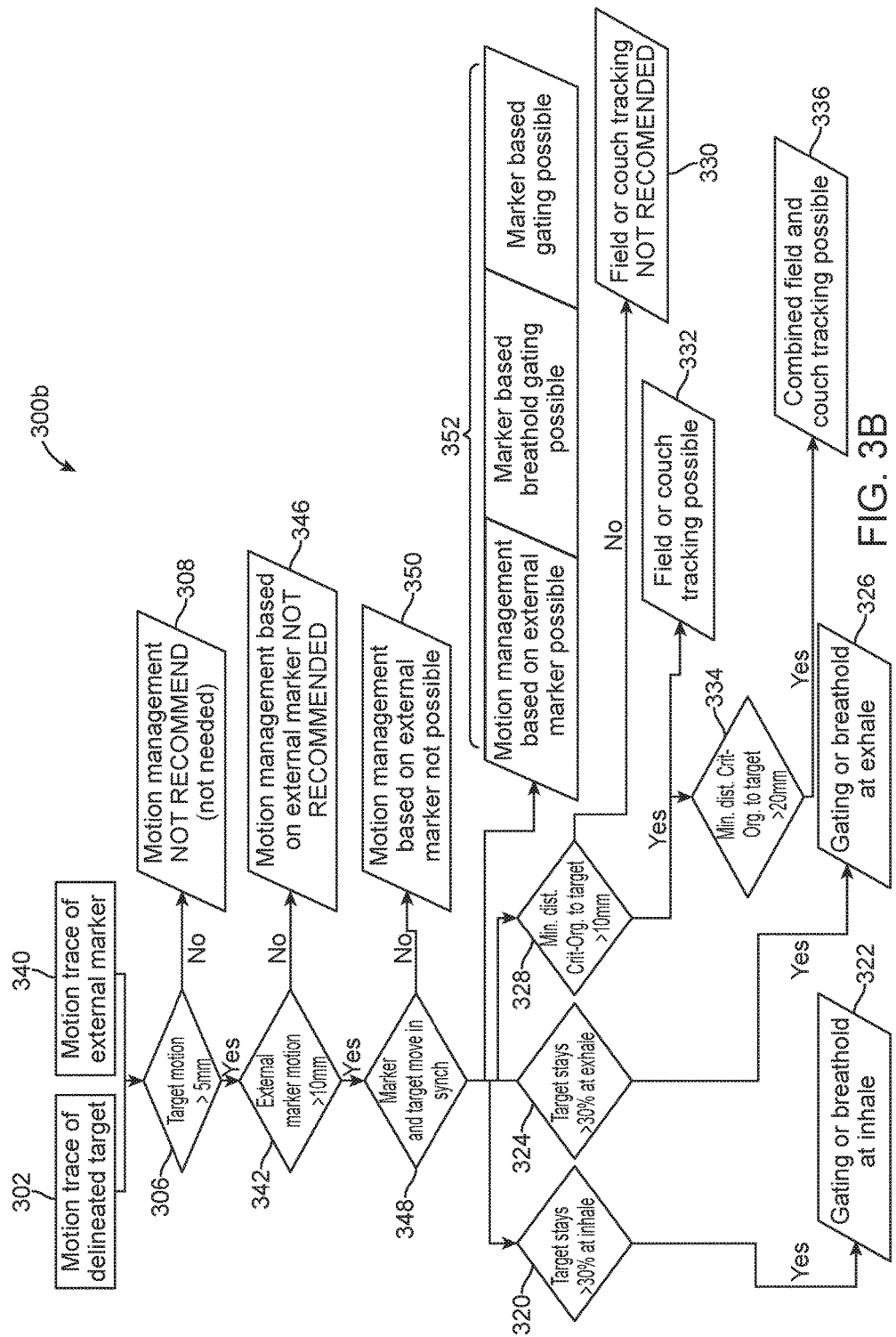
FIG. 3B illustrates another example of an algorithm.

FIG. 3B illustrates another example of an algorithm 300 that may be employed for providing motion management data that indicates a desirability and/or undesirability of one or more motion management option(s). The algorithm 300b of FIG. 3B is for determining whether one or more of the available motion management options are desirable for managing motion based on external marker(s) (one or more markers that are outside the patient) or patient surface. In one implementation, the external marker(s) may be implemented using the marker system described with reference to FIG. 1B. During use, the camera 102 may be used to view the marker block 104 having a plurality of markers. As the patient 28 breaths, the marker block 104 will move corresponding due to the breathing motion. The camera 102 captures the images of the marker block 104, and output the images in a sequence. The sequence of the images may itself be used as motion data of the marker(s), or alternatively may be used to derive positions of the marker(s) that constitute the motion data.

Referring to FIG. 3B, first, motion trace of a target is obtained (item 302), and motion data of marker(s) is obtained (item 340). In some embodiments, the motion trace of the target may be a sequence of images indicating motion of the target. In other embodiments, the motion trace may be positional data representing positions of the target over time. In addition, in some cases, the motion trace of the target may be obtained by analyzing a sequence of images to determine positions of the target in the respective images in the sequence. Also, in some embodiments, motion data of the marker(s) may be positional data of the marker(s) over time representing a motion of the marker(s). In some embodiments, items 302, 340 may be performed by an apparatus with one or more input(s) that receive the motion trace of the target and the motion data of the marker(s).

Next, the motion trace of the target is analyzed to determine whether a motion of the target is more than a prescribed target motion threshold (e.g., 5 mm in the example) (item 306). In other embodiments, the prescribed target motion threshold may be more than 5 mm or less than 5 mm. If the motion of the target is not greater than the prescribed target motion threshold, then the algorithm 300b may determine a motion management data indicating that no motion management is desirable (item 308). In some embodiments, item 306 may be performed by a target motion analyzer, which analyzes the motion trace of the target to determine if a motion amplitude is more than the prescribed target motion threshold (e.g., using a comparator).

If the motion of the target is greater than the prescribe target motion threshold, the algorithm 300b then determines whether a motion of the marker(s) is greater than a prescribed marker motion threshold by analyzing the motion data of the marker(s) (item 342). In the example, the prescribed marker motion threshold is 5 mm. In other embodiments, the prescribed marker motion threshold may be more than 5 mm or less than 5 mm. Also, the prescribed marker motion threshold may be the same as, or different from, the prescribe target motion threshold. In some embodiments, item 342 may be performed by a marker motion analyzer, which analyzes the motion data of the marker(s) to determine if a motion amplitude is more than the prescribed marker motion threshold (e.g., using a comparator). If the motion of the marker is not greater than the prescribed marker motion threshold, then the algorithm 300b may determine a motion management data indicating that motion management based on external marker(s) is undesirable (item 346).

If the motion of the marker(s) is greater than the prescribed marker motion threshold, then the algorithm 300b determines whether the motion of the marker(s) and the motion of the target are in synch (item 348). In some embodiments, item 348 may be performed by a synchronous motion detector, which analyzes the motion trace of the target and the motion data of the marker to determine if the target and the marker(s) move synchronously (e.g., using a waveform comparator). If the marker(s) and the target do not move synchronously with respect to each other, then the algorithm 300b may determine a motion management data indicating that motion management based on external marker is not desirable (item 350).

On the other hand, if the marker(s) and the target move synchronously with respect to each other (together with the satisfaction of the criteria that the target motion is greater than the target motion threshold, and the marker(s) motion is greater than the marker motion threshold), then the algorithm 300b may determine a motion management data indicating that several motion management options may be desirable (item 352). In the illustrated example, the algorithm 300b determines that motion management based on external marker(s), breath-hold gating based on external marker(s), and gating based on external marker(s), may be desirable.

In the illustrated example, the algorithm 300b further goes through several analyses to determine whether additional motion management option(s) may be desirable. In particular, the algorithm 300b may analyze the target motion to determine whether the target stays at a certain breathing phase (e.g., inhale) for more than a certain prescribed duration (e.g., 30%) (item 320). In some embodiments, item 320 may be performed by a target motion analyzer, which analyzes the motion trace of the target to determine how long the target stays within a certain breathing phase. If so, then the algorithm 300b may determine motion management data indicating that gating or breath-hold at the corresponding breathing phase (inhale in the example) may be desirable motion management option (item 322).

The algorithm 300b may also analyze the target motion to determine whether the target stays at another breathing phase (e.g., exhale) for more than a certain prescribed duration (e.g., 30%) (item 324). In some embodiments, item 324 may be performed by a target motion analyzer, which analyzes the motion trace of the target to determine how long the target stays within a certain breathing phase. If the target stays at the breathing phase for more than the prescribed duration, then the algorithm 300b may determine motion management data indicating that gating or breath-hold at the corresponding breathing phase (exhale in the example) may be desirable motion management option (item 326).

The algorithm 300b may also analyze image data to determine whether a minimum distance between the target and a critical organ is more than a first distance threshold (item 328). In some embodiments, item 328 may be performed by a distance analyzer, which measures a distance between the target and the critical organ, and compares the measured distance against the first distance threshold. If the minimum distance between the target and the critical organ is not more than the first distance threshold, then the algorithm 300b may determine motion management data indicating that field tracking and/or couch tracking is not desirable motion management option(s) (item 330). In other embodiments, if the minimum distance between the target and the critical organ is not more than the first distance threshold, then the algorithm 300a may determine motion management data indicating that field tracking and/or couch tracking is desirable motion management option(s). Optionally, if the minimum distance between the target and the critical organ is not more than the first distance threshold, the algorithm 300a may determine motion management data indicating that active beam steering is a desirable motion management option.

On the other hand, if the minimum distance between the target and the critical organ is more than the first distance threshold, then the algorithm 300b may determine motion management data indicating that field tracking and/or couch tracking may be a desirable motion management option (item 332).

The algorithm 300b may further determine whether the minimum distance between the target and the critical organ is more than a second distance threshold that is higher than the first distance threshold (item 334). In some embodiments, item 334 may be performed by a distance analyzer, which measures a distance between the target and the critical organ, and compares the measured distance against the second distance threshold. If the minimum distance between the target and the critical organ is more than the second distance threshold, then the algorithm 300b may determine motion management data indicating that combining field tracking and couch tracking may be a desirable motion management option (item 336).

It should be noted that in the algorithm 300b, there is no determination of whether the marker motion is visible from an imaging direction (like item 317 in the algorithm 300a). This is because when external marker(s) is used, the viewing camera 192 may be positioned so that it can view the marker(s). Thus, whether to check a criteria in an algorithm may be based on the type of fiducial and the technique employed to associate with target position.

Figure 3C:
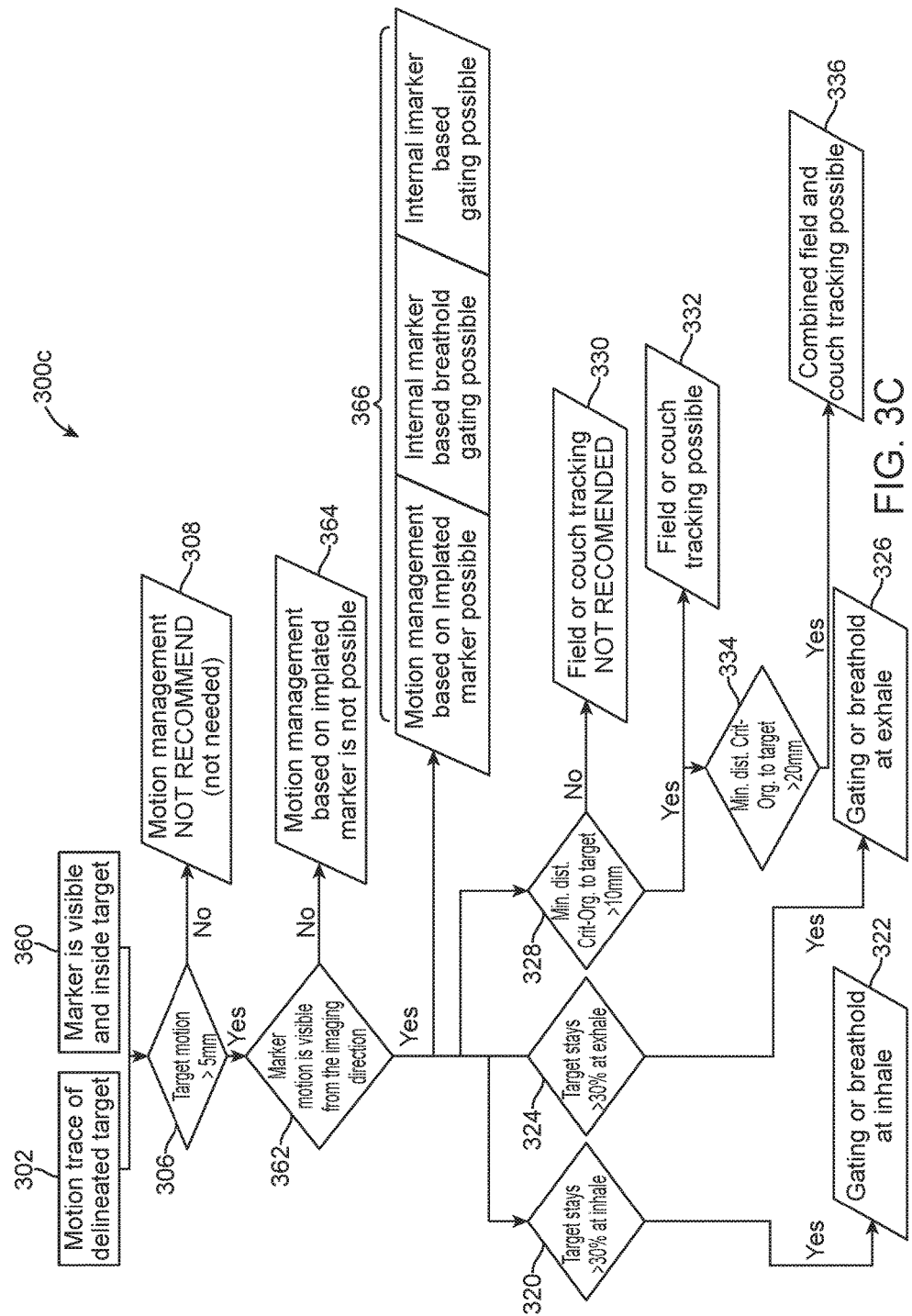
FIG. 3C illustrates another example of an algorithm.

FIG. 3C illustrates another example of an algorithm 300 that may be employed for providing motion management data that indicates a desirability and/or undesirability of one or more motion management option(s). The algorithm 300c of FIG. 3C is for determining whether one or more of the available motion management options are desirable for managing motion based on internal marker(s) (one or more markers that are inside the patient). An example of a medical system that utilizes internal marker for motion management is illustrated in FIG. 1C. In one implementation, the internal marker(s) may be implanted at the target. In the following description, it is assumed that the internal marker(s) are implanted at the target.

Referring to FIG. 3C, first, motion trace of a target is obtained (item 302), and motion data of internal marker(s) is obtained (item 360). In some embodiments, the motion trace of the target may be a sequence of images indicating motion of the target. In other embodiments, the motion trace may be positional data representing positions of the target over time. In addition, in some cases, the motion trace of the target may be obtained by analyzing a sequence of images to determine positions of the target in the respective images in the sequence. Also, in some embodiments, motion data of the internal marker(s) may be positional data of the internal marker(s) over time representing a motion of the internal marker(s). In some embodiments, items 302, 360 may be performed by an apparatus with one or more input(s) that receive the motion trace of the target and the motion data of the internal marker(s).

Next, the motion trace of the target is analyzed to determine whether a motion of the target is more than a prescribed target motion threshold (e.g., 5 mm in the example) (item 306). In other embodiments, the prescribed target motion threshold may be more than 5 mm or less than 5 mm. If the motion of the target is not greater than the prescribed target motion threshold, then the algorithm 300c may determine a motion management data indicating that no motion management is desirable (item 308). In some embodiments, item 306 may be performed by a target motion analyzer, which analyzes the motion trace of the target to determine if a motion amplitude is more than the prescribed target motion threshold (e.g., using a comparator).

If the motion of the target is greater than the prescribe target motion threshold, the algorithm 300c then determines whether the marker(s) motion is visible from an imaging direction (item 263). In some embodiments, item 263 may be performed by a visibility detector that determines an angle between a plane in which the marker(s) motion occurs and an imaging direction. If the angle is within a prescribed range (e.g., 90°±30°), then the algorithm 300c may determine that the marker(s) motion is visible from the imaging direction. In some embodiments, the imaging direction (with respect to certain coordinate system) may be input by a user. Also, in some embodiments, the plane in which the marker(s) motion occurs may be input by the user, or may be calculated automatically by the visibility detector. For example, the position of the plane relative to the certain coordinate system may be input by the user. Alternatively, if the position data of the marker(s) is with respect to another coordinate system, the visibility detector may transform the position data so that it is with respect to the same coordinate system as that of the imaging direction.

If the marker(s) motion is visible from the imaging direction, then the algorithm 300c may determine a motion management data indicating that several motion management options may be desirable (item 366). In the illustrated example, the algorithm 300c determines that motion management based on implanted marker(s), breath-hold gating based on implanted marker(s), and gating based on implanted marker(s), may be desirable.

In the illustrated example, the algorithm 300c further goes through several analyses to determine whether additional motion management option(s) may be desirable. In particular, the algorithm 300c may analyze the target motion to determine whether the target stays at a certain breathing phase (e.g., inhale) for more than a certain prescribed duration (e.g., 30%) (item 320). In some embodiments, item 320 may be performed by a target motion analyzer, which analyzes the motion trace of the target to determine how long the target stays within a certain breathing phase. If so, then the algorithm 300c may determine motion management data indicating that gating or breath-hold at the corresponding breathing phase (inhale in the example) may be desirable motion management option (item 322).

The algorithm 300c may also analyze the target motion to determine whether the target stays at another breathing phase (e.g., exhale) for more than a certain prescribed duration (e.g., 30%) (item 324). In some embodiments, item 324 may be performed by a target motion analyzer, which analyzes the motion trace of the target to determine how long the target stays within a certain breathing phase. If the target stays at the breathing phase for more than the prescribed duration, then the algorithm 300c may determine motion management data indicating that gating or breath-hold at the corresponding breathing phase (exhale in the example) may be desirable motion management option (item 326).

The algorithm 300c may also analyze image data to determine whether a minimum distance between the target and a critical organ is more than a first distance threshold (item 328). In some embodiments, item 328 may be performed by a distance analyzer, which measures a distance between the target and the critical organ, and compares the measured distance against the first distance threshold. If the minimum distance between the target and the critical organ is not more than the first distance threshold, then the algorithm 300c may determine motion management data indicating that field tracking and/or couch tracking is not desirable motion management option(s) (item 330). In other embodiments, if the minimum distance between the target and the critical organ is not more than the first distance threshold, then the algorithm 300a may determine motion management data indicating that field tracking and/or couch tracking is desirable motion management option(s). Optionally, if the minimum distance between the target and the critical organ is not more than the first distance threshold, the algorithm 300a may determine motion management data indicating that active beam steering is a desirable motion management option.

On the other hand, if the minimum distance between the target and the critical organ is more than the first distance threshold, then the algorithm 300c may determine motion management data indicating that field tracking and/or couch tracking may be a desirable motion management option (item 332).

The algorithm 300c may further determine whether the minimum distance between the target and the critical organ is more than a second distance threshold that is higher than the first distance threshold (item 334). In some embodiments, item 334 may be performed by a distance analyzer, which measures a distance between the target and the critical organ, and compares the measured distance against the second distance threshold. If the minimum distance between the target and the critical organ is more than the second distance threshold, then the algorithm 300c may determine motion management data indicating that combining field tracking and couch tracking may be a desirable motion management option (item 336).

It should be noted that in the algorithm 300c, there is no determination of whether the marker(s) motion is moving in sync with the target motion (like item 314 in the algorithm 300a). This is because when marker(s) is implanted at the target, the marker(s) will move synchronously with the target. Thus, whether to check a criteria in an algorithm may be based on the type of fiducial and the technique employed to associate with target position.

Figure 3D:
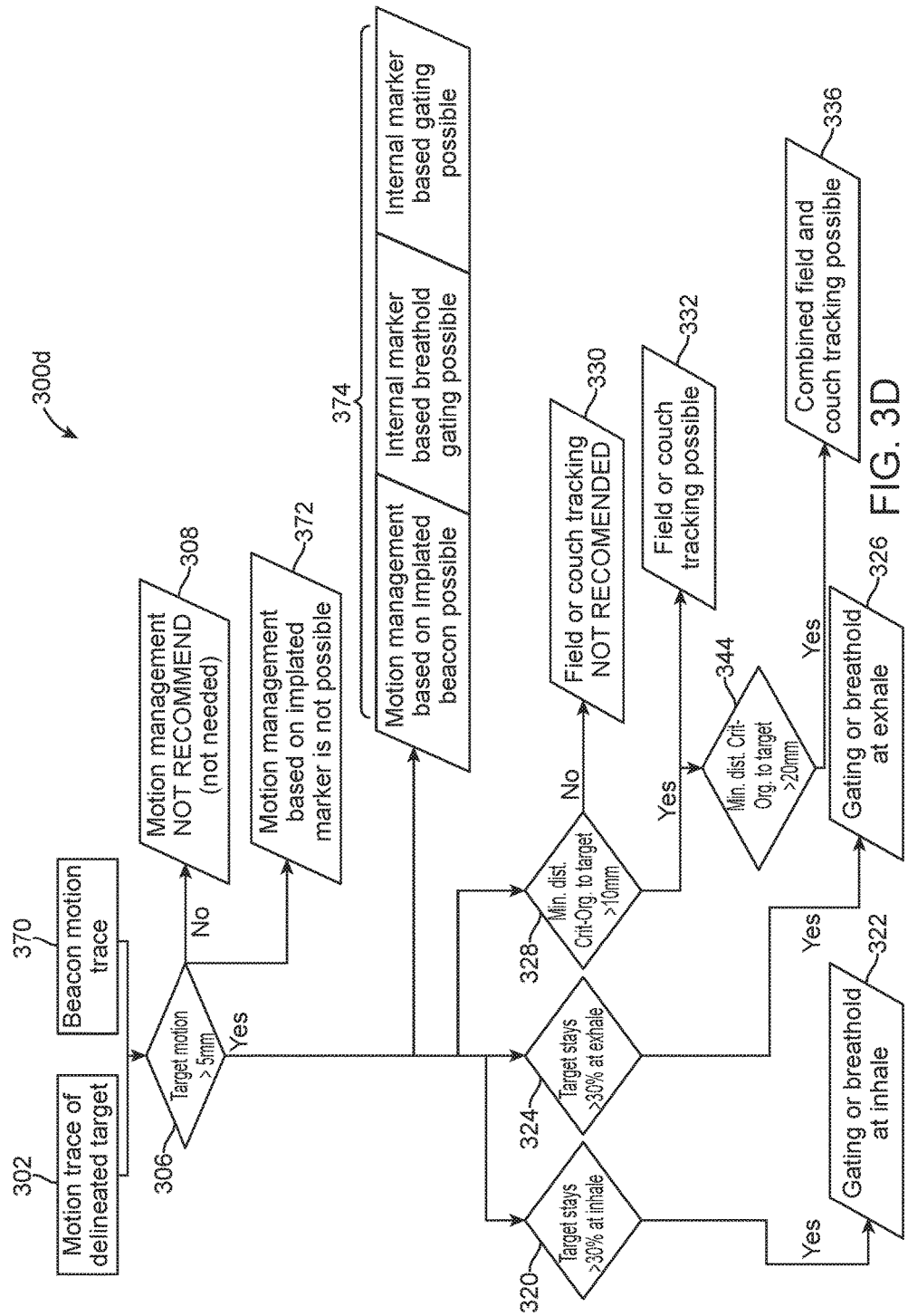
FIG. 3D illustrates another example of an algorithm.

FIG. 3D illustrates another example of an algorithm 300 that may be employed for providing motion management data that indicates a desirability and/or undesirability of one or more motion management option(s). The algorithm 300*d* of FIG. 3D is for determining whether one or more of the available motion management options are desirable for managing motion based on internal marker(s) that are in the form of beacon(s). An example of a medical system that utilizes beacon(s) for motion management is illustrated in FIG. 1D. In one implementation, the internal marker(s) (beacon(s) in this example) may be implanted at the target. In the following description, it is assumed that the internal marker(s) are beacon(s) and are implanted at the target. During use, the beacon(s) emits signals from inside the patient 28, which signals are then detected by a position signal detector outside the patient. The position signal detector may then determine the position of the beacon(s) based on a triangulation technique performed using the detected signals. By means of non-limiting examples, the beacon(s) may be configured to emit electromagnetic signals, ultrasound signals, radiofrequency signals, etc.

Referring to FIG. 3D, first, motion trace of a target is obtained (item 302), and motion data of internal marker(s) is obtained (item 370). In some embodiments, the motion trace of the target may be a sequence of images indicating motion of the target. In other embodiments, the motion trace may be positional data representing positions of the target over time. In addition, in some cases, the motion trace of the target may be obtained by analyzing a sequence of images to determine positions of the target in the respective images in the sequence. Also, in the illustrated embodiments, the marker(s) are internal beacon(s). Thus, the motion data of the internal marker(s) is in the form of beacon motion trace. In some cases, the motion data may be positional data of the internal beacon(s) over time representing a motion of the internal beacon(s). In some embodiments, items 302, 370 may be performed by an apparatus with one or more input(s) that receive the motion trace of the target and the motion data of the internal marker(s) (i.e., the motion trace of the beacon(s) in this example).

Next, the motion trace of the target is analyzed to determine whether a motion of the target is more than a prescribed target motion threshold (e.g., 5 mm in the example) (item 306). In other embodiments, the prescribed target motion threshold may be more than 5 mm or less than 5 mm. If the motion of the target is not greater than the prescribed target motion threshold, then the algorithm 300*d* may determine a motion management data indicating that no motion management is desirable (item 308). The algorithm 300*d* may also determine a motion management data indicating that motion management based on implanted beacon(s) is not desirable (item 372). In some embodiments, item 306 may be performed by a target motion analyzer, which analyzes the motion trace of the target to determine if a motion amplitude is more than the prescribed target motion threshold (e.g., using a comparator).

If the motion of the target is greater than the prescribe target motion threshold, the algorithm 300*d* may determine a motion management data indicating that several motion management options may be desirable (item 374). In the illustrated example, the algorithm 300*d* determines that motion management based on implanted beacon(s), breath-hold gating based on implanted beacon(s), and gating based on implanted beacon(s), may be desirable.

In the illustrated example, the algorithm 300*d* further goes through several analyses to determine whether additional motion management option(s) may be desirable. In particular, the algorithm 300*d* may analyze the target motion to determine whether the target stays at a certain breathing phase (e.g., inhale) for more than a certain prescribed duration (e.g., 30%) (item 320). In some embodiments, item 320 may be performed by a target motion analyzer, which analyzes the motion trace of the target to determine how long the target stays within a certain breathing phase. If so, then the algorithm 300*d* may determine motion management data indicating that gating or breath-hold at the corresponding breathing phase (inhale in the example) may be desirable motion management option (item 322).

The algorithm 300*d* may also analyze the target motion to determine whether the target stays at another breathing phase (e.g., exhale) for more than a certain prescribed duration (e.g., 30%) (item 324). In some embodiments, item 324 may be performed by a target motion analyzer, which analyzes the motion trace of the target to determine how long the target stays within a certain breathing phase. If the target stays at the breathing phase for more than the prescribed duration, then the algorithm 300*d* may determine motion management data indicating that gating or breath-hold at the corresponding breathing phase (exhale in the example) may be desirable motion management option (item 326).

The algorithm 300*d* may also analyze image data to determine whether a minimum distance between the target and a critical organ is more than a first distance threshold (item 328). In some embodiments, item 328 may be performed by a distance analyzer, which measures a distance between the target and the critical organ, and compares the measured distance against the first distance threshold. If the minimum distance between the target and the critical organ is not more than the first distance threshold, then the algorithm 300*d* may determine motion management data indicating that field tracking and/or couch tracking is not desirable motion management option(s) (item 330). In other embodiments, if the minimum distance between the target and the critical organ is not more than the first distance threshold, then the algorithm 300*a* may determine motion management data indicating that field tracking and/or couch tracking is desirable motion management option(s). Optionally, if the minimum distance between the target and the critical organ is not more than the first distance threshold, the algorithm 300*a* may determine motion management data indicating that active beam steering is a desirable motion management option.

On the other hand, if the minimum distance between the target and the critical organ is more than the first distance threshold, then the algorithm 300*d* may determine motion management data indicating that field tracking and/or couch tracking may be a desirable motion management option (item 332).

The algorithm 300*d* may further determine whether the minimum distance between the target and the critical organ is more than a second distance threshold that is higher than the first distance threshold (item 334). In some embodiments, item 334 may be performed by a distance analyzer, which measures a distance between the target and the critical organ, and compares the measured distance against the second distance threshold. If the minimum distance between the target and the critical organ is more than the second distance threshold, then the algorithm 300*d* may determine motion management data indicating that combining field tracking and couch tracking may be a desirable motion management option (item 336).

It should be noted that in the algorithm 300*d*, there is no determination of whether the beacon(s) motion is moving in sync with the target motion (like item 314 in the algorithm 300*a*). This is because when the beacon(s) is implanted at or close to the target, the beacon(s) will move synchronously with the target. Also, in the algorithm 300*d*, there is no determination of whether the beacon(s) motion is larger than a prescribed beacon motion threshold (like item 310 in the algorithm 300*a*). This is because beacon(s) may provide relatively more accurate positioning. Accordingly, even if the beacon(s) motion is not significant (i.e., less than a prescribed threshold), the beacon(s) position may still be used to correlate with target position. Furthermore, in the algorithm 300*d*, there is no determination of whether the beacon(s) is visible from a certain imaging direction. This is because positioning technique using beacon(s) is achieved based on signals emitted by the beacon(s) and triangulation of those signals, and there is no need to perform any imaging of the beacon(s). Accordingly, whether to check a criteria in an algorithm may be based on the type of fiducial and the technique employed to associate with target position.

Figure 3E:
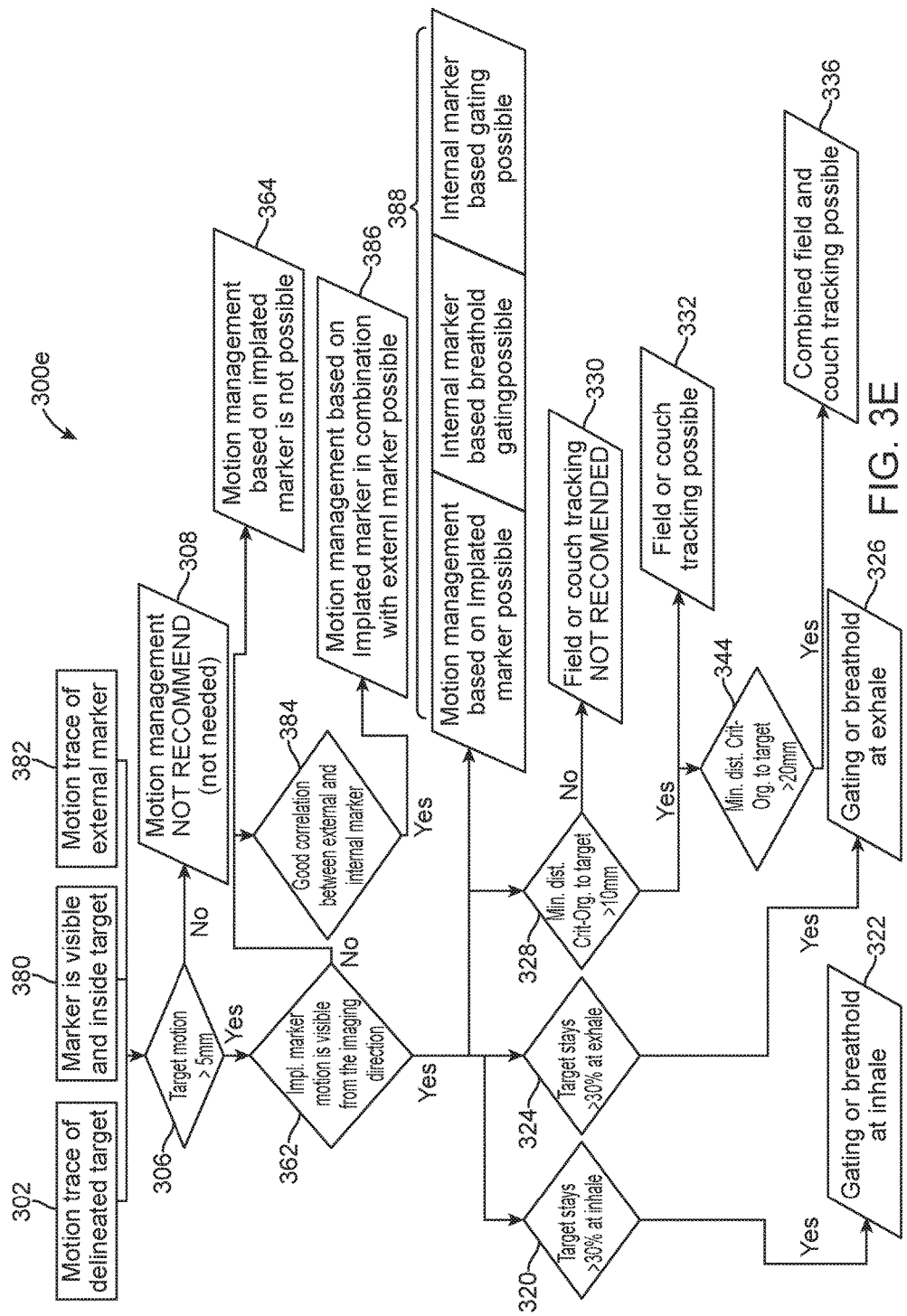
FIG. 3E illustrates another example of an algorithm.

FIG. 3E illustrates another example of an algorithm 300 that may be employed for providing motion management data that indicates a desirability and/or undesirability of one or more motion management option(s). The algorithm 300*e* of FIG. 3E is for determining whether one or more of the available motion management options are desirable for managing motion based on an internal marker(s) and/or external marker(s). An example of a medical system that utilizes internal marker(s) and/or external marker(s) for motion management is illustrated in FIG. 1E. In the example of FIG. 3E, the internal marker(s) is implanted at the target, and is configured to be imaged by an imaging device during a treatment procedure. The imaging device may be a x-ray machine, a CT machine, a MRI machine, an ultrasound device, a portal imager that is attached to a treatment machine, etc.

Also, in one implementation, the external marker(s) may be implemented using the marker system described with reference to FIG. 1. During use, the camera 102 may be used to view the marker block 104 having a plurality of markers. As the patient 28 breaths, the marker block 104 will move correspondingly due to the breathing motion. The camera 102 captures the images of the marker block 104, and output the images in a sequence. The sequence of the images may itself be used as motion data of the marker(s), or alternatively may be used to derive positions of the marker(s) that constitute the motion data.

First, motion trace of a target is obtained (item 302), motion data of internal marker(s) is obtained (item 380), and motion data of external marker(s) is obtained (item 382). In some embodiments, the motion trace of the target may be a sequence of images indicating motion of the target. In other embodiments, the motion trace may be positional data representing positions of the target over time. In addition, in some cases, the motion trace of the target may be obtained by analyzing a sequence of images to determine positions of the target in the respective images in the sequence. Also, in some embodiments, motion data of the internal marker(s) may be positional data of the internal marker(s) over time representing a motion of the internal marker(s). Similarly, in some embodiments, motion data of the external marker(s) may be positional data of the external marker(s) over time representing a motion of the external marker(s). In some embodiments, items 302, 380, 382 may be performed by an apparatus with one or more input(s) that receive the motion trace of the target, the motion data of the internal marker(s), and the motion data of the external marker(s).

Next, the motion trace of the target is analyzed to determine whether a motion of the target is more than a prescribed target motion threshold (e.g., 5 mm in the example) (item 306). In other embodiments, the prescribed target motion threshold may be more than 5 mm or less than 5 mm. If the motion of the target is not greater than the prescribed target motion threshold, then the algorithm 300*e* may determine a motion management data indicating that no motion management is desirable (item 308). In some embodiments, item 306 may be performed by a target motion analyzer, which analyzes the motion trace of the target to determine if a motion amplitude is more than the prescribed target motion threshold (e.g., using a comparator).

If the motion of the target is greater than the prescribe target motion threshold, the algorithm 300*e* then determines whether a motion of the internal marker(s) is visible from an imaging direction (item 362). In some embodiments, item 362 may be performed by a visibility detector that determines an angle between a plane in which the marker(s) motion occurs and an imaging direction. If the angle is within a prescribed range (e.g., 90°±30°), then the algorithm 300*e* may determine that the internal marker(s) motion is visible from the imaging direction. In some embodiments, the imaging direction (with respect to certain coordinate system) may be input by a user. Also, in some embodiments, the plane in which the internal marker(s) motion occurs may be input by the user, or may be calculated automatically by the visibility detector. For example, the position of the plane relative to the certain coordinate system may be input by the user. Alternatively, if the position data of the surrogate is with respect to another coordinate system, the visibility detector may transform the position data so that it is with respect to the same coordinate system as that of the imaging direction.

If the internal marker(s) motion is not visible from the imaging direction, then it may still be possible to use the external marker(s) or the detected patient surface as a surrogate for determining the position of the target provided that there is a good correlation between the external marker(s) and the internal marker(s). Accordingly, the algorithm 300*e* determines whether there is a good (e.g., sufficient) correlation between the external marker(s) and the internal marker(s) in item 384. In some embodiments, the correlation between the external marker(s) and the internal marker(s) may be considered sufficient if the external marker(s) motion is in sync with the internal marker(s) motion. In one implementation, a comparator may analyze (e.g., compare) the external and internal markers motions to determine if the two motions are in sync. The comparator may calculate a correlation value representing a degree of similarity between the two motions. In some cases, amplitude values of each of the two motions may be normalized before the two motions are compared. In some embodiments, the two motions may be considered to be in sync if the correlation value is higher than a prescribed threshold, such as 0.6, and more preferably 0.7, and even more preferably 0.8, and even more preferably 0.9.

If the algorithm 300*e* determines that there is insufficient correlation, the algorithm 300*e* may then determine a motion management data indicating that motion management based on internal marker(s) is not desirable (item 364). If the algorithm 300*e* determines that there is sufficient correlation, the algorithm 300*e* may then determine a motion management data indicating that motion management based on internal marker(s) in combination with external marker(s) is desirable (item 386).

Returning to item 362, if the internal marker(s) motion is visible from the imaging direction, then the algorithm 300*e* may determine a motion management data indicating that several motion management options that do not require external marker(s) may be desirable (item 386). In the illustrated example, the algorithm 300*e* determines that motion management based on internal marker(s), breath-hold gating based on internal marker(s), and gating based on internal marker(s), may be desirable.

In the illustrated example, the algorithm 300*e* further goes through several analyses to determine whether additional motion management option(s) may be desirable. In particular, the algorithm 300*e* may analyze the target motion to determine whether the target stays at a certain breathing phase (e.g., inhale) for more than a certain prescribed duration (e.g., 30%) (item 320). In some embodiments, item 320 may be performed by a target motion analyzer, which analyzes the motion trace of the target to determine how long the target stays within a certain breathing phase. If so, then the algorithm 300*e* may determine motion management data indicating that gating or breath-hold at the corresponding breathing phase (inhale in the example) may be desirable motion management option (item 322).

The algorithm 300*e* may also analyze the target motion to determine whether the target stays at another breathing phase (e.g., exhale) for more than a certain prescribed duration (e.g., 30%) (item 324). In some embodiments, item 324 may be performed by a target motion analyzer, which analyzes the motion trace of the target to determine how long the target stays within a certain breathing phase. If the target stays at the breathing phase for more than the prescribed duration, then the algorithm 300*e* may determine motion management data indicating that gating or breath-hold at the corresponding breathing phase (exhale in the example) may be desirable motion management option (item 326).

The algorithm 300*e* may also analyze image data to determine whether a minimum distance between the target and a critical organ is more than a first distance threshold (item 328). In some embodiments, item 328 may be performed by a distance analyzer, which measures a distance between the target and the critical organ, and compares the measured distance against the first distance threshold. If the minimum distance between the target and the critical organ is not more than the first distance threshold, then the algorithm 300*e* may determine motion management data indicating that field tracking and/or couch tracking is not desirable motion management option(s) (item 330). In other embodiments, if the minimum distance between the target and the critical organ is not more than the first distance threshold, then the algorithm 300*a* may determine motion management data indicating that field tracking and/or couch tracking is desirable motion management option(s). Optionally, if the minimum distance between the target and the critical organ is not more than the first distance threshold, the algorithm 300*a* may determine motion management data indicating that active beam steering is a desirable motion management option.

On the other hand, if the minimum distance between the target and the critical organ is more than the first distance threshold, then the algorithm 300*e* may determine motion management data indicating that field tracking and/or couch tracking may be a desirable motion management option (item 332).

The algorithm 300*e* may further determine whether the minimum distance between the target and the critical organ is more than a second distance threshold that is higher than the first distance threshold (item 334). In some embodiments, item 334 may be performed by a distance analyzer, which measures a distance between the target and the critical organ, and compares the measured distance against the second distance threshold. If the minimum distance between the target and the critical organ is more than the second distance threshold, then the algorithm 300*e* may determine motion management data indicating that combining field tracking and couch tracking may be a desirable motion management option (item 336).

Figure 4:
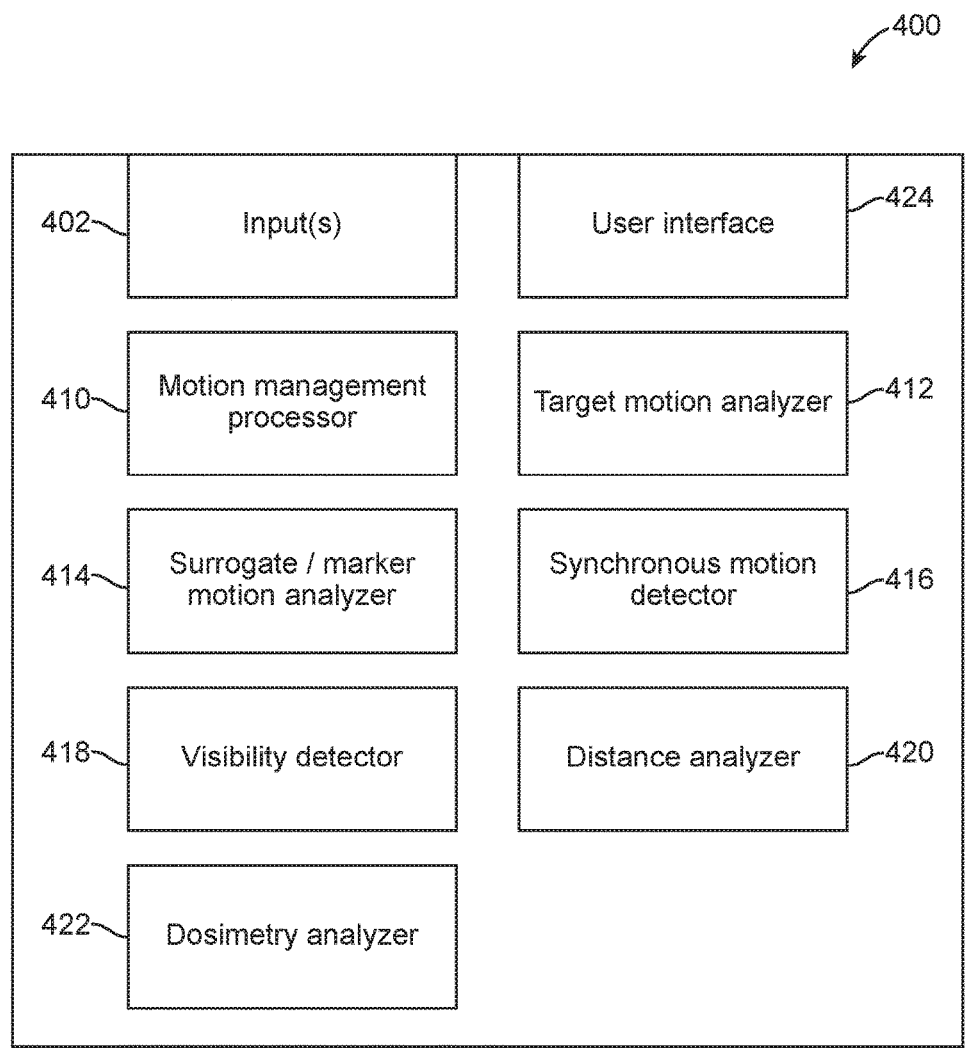
FIG. 4 illustrates an apparatus in accordance with some embodiments.

FIG. 4 illustrates an apparatus 400 for assisting a selection of motion management technique for use with a treatment machine having an energy source. The apparatus 400 may implement or utilize one, some, or all, of the algorithms 300*a*-300*e* described with reference to FIGS. 3A-3E. In other embodiments, the apparatus 400 may implement other algorithm(s). Referring to FIG. 4, the apparatus 400 includes one or more input 402 for obtaining motion trace of a target in a patient to be treated, and for obtaining motion data of a fiducial. The apparatus 400 also includes a motion management processor 410 configured to determine motion management data based at least in part on at least a portion of the motion trace of the target and at least a portion of the motion data of the fiducial, wherein the motion management data indicates desirability and/or undesirability of one or more motion management option(s). The motion management processor 410 is also configured to output the motion management data for assisting the selection of the motion management technique for use with the treatment machine.

Optionally, the apparatus 400 further includes a target motion analyzer 412 configured to determine whether a motion of the target is more than a prescribed amount.

The prescribed amount may be a prescribed distance (e.g., amplitude) or a prescribed phase of a motion. Thus, a motion of the target may be considered as being more than a prescribed amount if it motion amplitude exceeds a prescribed amplitude, or if its motion phase exceeds the prescribed phase.

Optionally, the motion management data indicates that no motion management option is desirable if the motion of the target is less than the prescribed amount.

Optionally, the fiducial comprises a surrogate inside the patient.

Optionally, the apparatus 400 further includes a surrogate motion analyzer 414 configured to determine whether a motion of the surrogate is more than a prescribed amount, wherein the motion management data indicates that no motion management is desirable if the motion of the surrogate is less than the prescribed amount.

Optionally, the fiducial comprises a surrogate inside the patient, and the apparatus 400 further comprises a synchronous motion detector 416 configured to determine whether the surrogate moves synchronously with the target.

Optionally, the motion management data indicates motion management based on surrogate is undesirable if the surrogate does not move synchronously with the target.

Optionally, the fiducial comprises a marker coupled to the patient, and the apparatus 400 further comprises a synchronous motion detector 416 configured to determine whether the marker moves synchronously with the target.

Optionally, the motion management data indicates that motion management based on the marker is undesirable if the marker does not move synchronously with the target.

Optionally, the fiducial comprises a marker, and the apparatus 400 further comprises a visibility detector 418 configured to determine whether a motion of the marker is visible from an imaging direction; and wherein the motion management processor is configured to determine the motion management data based at least in part on whether the motion of the marker is visible from the imaging direction. In other cases, instead of the marker, an anatomical surrogate may be used.

Optionally, the apparatus 400 further includes a target motion analyzer 412 configured to determine whether the target stays at an inhale phase for more than a prescribed duration, wherein the motion management processor 410 is configured to determine the motion management data based at least in part on whether the target stays at the inhale phase for more than the prescribed duration.

Optionally, the motion management data indicates that gating-at-inhale and breath-hold-at-inhale are desirable motion management options if the target stays at the inhale phase for more than the prescribed duration.

Optionally, the apparatus 400 further includes a target motion analyzer 412 configured to determine whether the target stays at an exhale phase for more than a prescribed duration, wherein the motion management processor 410 is configured to determine the motion management data based at least in part on whether the target stays at the exhale phase for more than the prescribed duration.

Optionally, the motion management data indicates that gating-at-exhale and breath-hold-at-exhale are desirable motion management options if the target stays at the exhale phase for more than the prescribed duration.

Optionally, the apparatus 400 further includes a distance analyzer 420 configured to determine whether a distance between the target and a critical organ is more than a first threshold.

Optionally, the motion management data indicates that field-tracking and/or couch-tracking is desirable motion management option(s) or not if the distance between the target and the critical organ is not more than the first threshold.

Optionally, the apparatus 400 further includes a distance analyzer 400 configured to determine whether the distance between the target and the critical organ is more than a second threshold that is larger than the first threshold.

Optionally, the motion management data indicates that field-tracking and/or couch-tracking is a desirable motion management option if the distance between the target and the critical organ is not more than the second threshold.

Optionally, the motion management data indicates that field-tracking in combination with couch-tracking is a desirable motion management option if the distance between the target and the critical organ is more than the second threshold.

Optionally, the apparatus 400 further includes a display for displaying the motion management data.

Optionally, the motion trace comprises a segmentation of the target.

Optionally, the motion management processor 410 is configured to provide the motion management data to a treatment planning module.

Optionally, the one or more input 402 is also configured to obtain a signal input representing a change of one or more parameters involved in a treatment planning; and wherein the motion management processor 410 is configured to perform calculation using the input to obtain new motion management data.

Optionally, the motion trace comprise a video formed by CT image data, MRI data, or x-ray image data.

Optionally, the motion data represents a real motion or a simulated motion.

Optionally, the motion trace, the motion data, or both, are data generated during a treatment session.

Optionally, the motion management processor 410 is configured to determine the motion management data based also on data generated during the treatment session.

Optionally, the apparatus 400 further includes dosimetry analyzer 422 configured to determine dosimetry impact of one or more of the motion management option(s).

Optionally, the motion management processor 410 is configured to analyze the motion trace and the motion data to determine whether a plurality of criteria is met; wherein the motion management processor 410 is configured to determine the motion management data based on a result of the analyzing.

Optionally, the motion management processor 410 is configured to classify a first subset of all available motion management options as desirable motion management option(s), and to classify a second subset of the available motion management options as undesirable motion management option(s) based on the result of the analyzing.

Optionally, the motion management data also indicates one or more of: an amount of movement of the target over a breathing cycle, an amount of movement of the target inside a percentage of a breathing amplitude, an amount of movement of the target over a certain phase range of a breathing cycle, gantry angle(s) or a range of gantry angles at or over which a distance between the target and a critical structure is less than a prescribed value, a duration for which the target does not shift by more than a prescribed distance during an exhale phase, a duration for which the target does not shift by more than a prescribed distance during an inhale phase, motion information regarding an organ at risk, an amount of movement of a critical organ over a breathing cycle, an amount of movement of the critical organ inside a percentage of a breathing amplitude, an amount of movement of the critical organ over a certain phase range of the breathing cycle, a duration for which the critical organ does not shift by more than a prescribed distance during the exhale phase, a duration for which the critical organ does not shift by more than a prescribed distance during the inhale phase, dose volume parameter that depends on a chosen motion management scheme, an estimated treatment time, dose robustness measure based on motion variability, or any combination of the foregoing.

Optionally, the motion management data comprises one or more setting recommendations selected from the group consisting of: gating window for performing gating of radiation deliveries, gating window at different gantry angles, a change in gating window(s) depending on angles or angle segments, tracking parameter(s) for MLC or couch, optimal collimator settings at different gantry positions, and parameter suggestion for predicting motion.

Optionally, the motion management technique corresponds with one of the one or more motion management option(s).

In some embodiments, the apparatus 400 may also include a user interface 424 for receiving an input from a user. For example, the input may include any information for defining one or more of the criteria in the algorithms 300a-300e described with reference to FIGS. 3A-3E. By means of non-limiting examples, the input may include one or more of a target motion threshold, a fiducial motion threshold, one or more distance thresholds, one or more selected phases of a breathing cycle, a first minimum distance (between critical organ and target) criteria, a second minimum distance criteria. The user interface 424 may also receive an input from a user indicating the type of system (e.g., internal fiducial, external marker, implanted marker, beacon, etc.) for monitoring motion for motion management. The user interface may also be configured to receive motion trace of a target.

Also, in some embodiments, the user interface may include a window presenting a two-dimensional x-ray video, which allows the user to see the motion of internal objects. The video may be a previously recorded video, or may be live images obtained in real time. In other embodiments, instead of a x-ray video, the user interface may present a video of other types of imaging (e.g., a video of ultrasound images, MRI images, CT images, etc.).

In some embodiments, the apparatus 400 may comprise a specialized processor configured with thresholds described herein, and also with an logic to carry out one or more features described herein.

Figure 5:
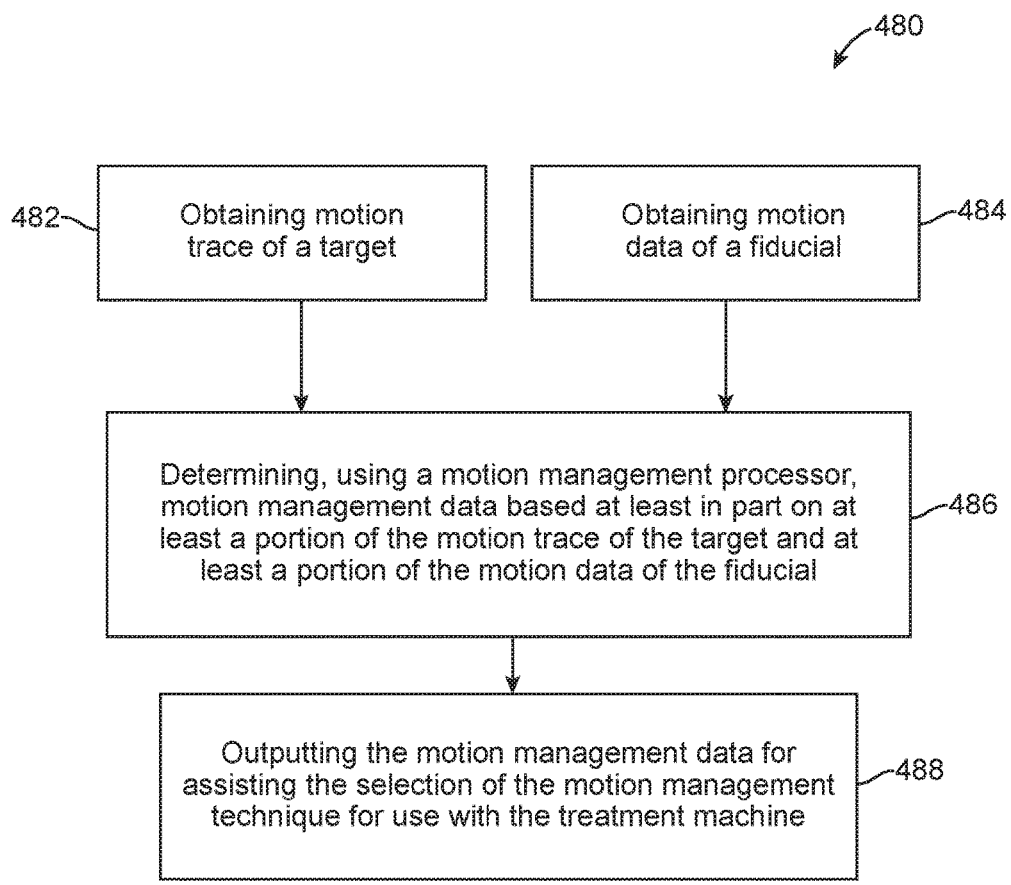
FIG. 5 illustrates a method in accordance with some embodiments.

FIG. 5 illustrates a processor-implemented method 480 for assisting a selection of motion management technique for use with a treatment machine having an energy source. The method 480 may implement or utilize one, some, or all, of the algorithms 300a-300e described with reference to FIGS. 3A-3E. Also, in some embodiments, the method 480 may be performed by the apparatus 400 of FIG. 4, or by another apparatus. The method 480 includes obtaining motion trace of a target in a patient to be treated (item 482), and/or obtaining motion data of a fiducial (item 484). The method 480 also includes determining, using a motion management processor, motion management data based at least in part on at least a portion of the motion trace of the target and at least a portion of the motion data of the fiducial (item 486). In some cases, the motion management data indicates desirability and/or undesirability of one or more motion management option(s). The method 480 also includes outputting the motion management data for assisting the selection of the motion management technique for use with the treatment machine (item 488).

Optionally, the method 480 further includes determining whether a motion of the target is more than a prescribed amount.

Optionally, the motion management data indicates that no motion management option is desirable if the motion of the target is less than the prescribed amount.

Optionally, the fiducial comprises on a surrogate inside the patient.

Optionally, the method 480 further includes determining whether a motion of the surrogate is more than a prescribed amount, wherein the motion management data indicates that no motion management is desirable if the motion of the surrogate is less than the prescribed amount.

Optionally, the fiducial comprises a surrogate inside the patient, and the method 480 further comprises determining whether the surrogate moves synchronously with the target.

Optionally, the motion management data indicates motion management based on surrogate is undesirable if the surrogate does not move synchronously with the target.

Optionally, the fiducial comprises a marker coupled to the patient, and the method 480 further comprises determining whether the marker moves synchronously with the target.

Optionally, the motion management data indicates that motion management based on the marker is undesirable if the marker does not move synchronously with the target.

Optionally, the fiducial comprises a marker, and the method 480 further comprises determining whether a motion of the marker is visible from an imaging direction; and wherein the motion management data is determined based at least in part on whether the motion of the marker is visible from the imaging direction.

Optionally, the method 480 further includes determining whether the target stays at an inhale phase for more than a prescribed duration, wherein the motion management data is determined based at least in part on whether the target stays at the inhale phase for more than the prescribed duration.

Optionally, the motion management data indicates that gating-at-inhale and breath-hold-at-inhale are desirable motion management options if the target stays at the inhale phase for more than the prescribed duration.

Optionally, the method 480 further includes determining whether the target stays at an exhale phase for more than a prescribed duration, wherein the motion management data is determined based at least in part on whether the target stays at the exhale phase for more than the prescribed duration.

Optionally, the motion management data indicates that gating-at-exhale and breath-hold-at-exhale are desirable motion management options if the target stays at the exhale phase for more than the prescribed duration.

Optionally, the method 480 further includes determining whether a distance between the target and a critical organ is more than a first threshold.

Optionally, the motion management data indicates that field-tracking and/or couch-tracking is desirable motion management option(s) or not if the distance between the target and the critical organ is not more than the first threshold.

Optionally, the method 480 further includes determining whether the distance between the target and the critical organ is more than a second threshold that is larger than the first threshold.

Optionally, the motion management data indicates that field-tracking and/or couch-tracking is a desirable motion management option if the distance between the target and the critical organ is not more than the second threshold.

Optionally, the motion management data indicates that field-tracking in combination with couch-tracking is a desirable motion management option if the distance between the target and the critical organ is more than the second threshold.

Optionally, the method 480 further includes displaying the motion management data.

Optionally, the motion trace comprises a segmentation of the target.

Optionally, the method 480 further includes providing the motion management data, by a motion management module, to a treatment planning module.

Optionally, the method 480 further includes: obtaining input representing a change of one or more parameters involved in a treatment planning; and performing calculation using the input to obtain new motion management data.

Optionally, the act of obtaining input and the act of performing calculation using the input are repeated.

Optionally, the motion trace comprise a video formed by CT image data, MRI data, or x-ray image data.

Optionally, the motion data represents a real motion or a simulated motion.

Optionally, the motion trace, the motion data, or both, are data generated during a treatment session.

Optionally, the method 480 further includes obtaining data generated during a treatment session, wherein the motion management data is determined based also on the data generated during the treatment session.

Optionally, the method 480 further includes determining dosimetry impact of one or more of the motion management option(s).

Optionally, the method 480 further includes analyzing the motion trace and the motion data to determine whether a plurality of criteria is met; wherein the motion management data is determined based on a result of the analyzing.

Optionally, the method 480 further includes classifying a first subset of all available motion management options as desirable motion management option(s), and classifying a second subset of the available motion management options as undesirable motion management option(s) based on the result of the analyzing.

Optionally, the motion management data also indicates one or more of: an amount of movement of the target over a breathing cycle, an amount of movement of the target inside a percentage of a breathing amplitude, an amount of movement of the target over a certain phase range of a breathing cycle, gantry angle(s) or a range of gantry angles at or over which a distance between the target and a critical structure is less than a prescribed value, a duration for which the target does not shift by more than a prescribed distance during an exhale phase, a duration for which the target does not shift by more than a prescribed distance during an inhale phase, motion information regarding an organ at risk, an amount of movement of a critical organ over a breathing cycle, an amount of movement of the critical organ inside a percentage of a breathing amplitude, an amount of movement of the critical organ over a certain phase range of the breathing cycle, a duration for which the critical organ does not shift by more than a prescribed distance during the exhale phase, a duration for which the critical organ does not shift by more than a prescribed distance during the inhale phase, dose volume parameter that depends on a chosen motion management scheme, an estimated treatment time, dose robustness measure based on motion variability, or any combination of the foregoing.

Optionally, the motion management data comprises one or more setting recommendations selected from the group consisting of: gating window for performing gating of radiation deliveries, gating window at different gantry angles, a change in gating window(s) depending on angles or angle segments, tracking parameter(s) for MLC or couch, optimal collimator settings at different gantry positions, and parameter suggestion for predicting motion.

Optionally, the motion management technique corresponds with one of the one or more motion management option(s).

FIGS. 6A-6E illustrate examples of data structures that may be used by the apparatus 400 and/or the method 480.

FIG. 6A illustrates a data structure 600*a* that may be used with the system of FIG. 1A. The data structure 600*a* may also be used to implement the algorithm of FIG. 3A. As shown in FIG. 6A, the data structure 600*a* includes a plurality of criteria (in different columns) that correspond with the criteria described with reference to the algorithm 300*a* of FIG. 3A. The data structure 600*a* also includes a plurality of motion management options in different rows. In other embodiments, the criteria may be arranged in different rows, and the different motion management motions may be arranged in different columns. As shown in the example, the data structure 600*a* includes flags "Y" that represents a satisfaction of a certain criterion. For example, a "Y" under the criteria "Target motion>5 mm" indicates that such criterion is satisfied. In order for a certain motion management option to be considered desirable, the criteria with the flag "Y" needs to be met. For example, referring to the first motion management option "motion management based on internal surrogate" in the data structure 600*a*, in order for the apparatus 400 to recommend this motion management option, the four criteria with the flag "Y" (in the first row) need to be met. The same is true for the other motion management options. During use, the apparatus 400 determines whether the criteria listed in the data structure 600*a* are met. Then the apparatus 400 accesses the data structure 600*a*, and compare the satisfied criteria with those listed in the data structure 600*a*. The apparatus 400 may then output motion management data indicating which of the available motion management options are desirable based on the comparison.

FIG. 6B illustrates a data structure 600*b* that may be used with the system of FIG. 1B. The data structure 600*b* may also be used to implement the algorithm of FIG. 3B. As shown in FIG. 6B, the data structure 600*b* includes a plurality of criteria (in different columns) that correspond with the criteria described with reference to the algorithm 300*b* of FIG. 3B. The data structure 600*b* also includes a plurality of motion management options in different rows. In other embodiments, the criteria may be arranged in different rows, and the different motion management motions may be arranged in different columns. As shown in the example, the data structure 600*b* includes flags "Y" that represents a satisfaction of a certain criterion. For example, a "Y" under the criteria "Target motion>5 mm" indicates that such criterion is satisfied. In order for a certain motion management option to be considered desirable, the criteria with the flag "Y" needs to be met. For example, referring to the first motion management option "motion management based on external marker" in the data structure 600*b*, in order for the apparatus 400 to recommend this motion management option, the four criteria with the flag "Y" (in the first row) need to be met. The same is true for the other motion management options. During use, the apparatus 400 determines whether the criteria listed in the data structure 600*b* are met. Then the apparatus 400 accesses the data structure 600*b*, and compare the satisfied criteria with those listed in the data structure 600*b*. The apparatus 400 may then output motion management data indicating which of the available motion management options are desirable based on the comparison.

FIG. 6C illustrates a data structure 600*c* that may be used with the system of FIG. 1C. The data structure 600*a* may also be used to implement the algorithm of FIG. 3C. As shown in FIG. 6C, the data structure 600*c* includes a plurality of criteria (in different columns) that correspond with the criteria described with reference to the algorithm 300*c* of FIG. 3C. The data structure 600*c* also includes a plurality of motion management options in different rows. In other embodiments, the criteria may be arranged in different rows, and the different motion management motions may be arranged in different columns. As shown in the example, the data structure 600*c* includes flags "Y" that represents a satisfaction of a certain criterion. For example, a "Y" under the criteria "Target motion>5 mm" indicates that such criterion is satisfied. In order for a certain motion management option to be considered desirable, the criteria with the flag "Y" needs to be met. For example, referring to the first motion management option "motion management based on implanted marker" in the data structure 600*c*, in order for the apparatus 400 to recommend this motion management option, the two criteria with the flag "Y" (in the first row) need to be met. The same is true for the other motion management options. During use, the apparatus 400 determines whether the criteria listed in the data structure 600*c* are met. Then the apparatus 400 accesses the data structure 600c, and compare the satisfied criteria with those listed in the data structure 600c. The apparatus 400 may then output motion management data indicating which of the available motion management options are desirable based on the comparison.

FIG. 6D illustrates a data structure 600d that may be used with the system of FIG. 1D. The data structure 600a may also be used to implement the algorithm of FIG. 3D. As shown in FIG. 6D, the data structure 600d includes a plurality of criteria (in different columns) that correspond with the criteria described with reference to the algorithm 300d of FIG. 3D. The data structure 600d also includes a plurality of motion management options in different rows. In other embodiments, the criteria may be arranged in different rows, and the different motion management motions may be arranged in different columns. As shown in the example, the data structure 600d includes flags "Y" that represents a satisfaction of a certain criterion. For example, a "Y" under the criteria "Target motion>5 mm" indicates that such criterion is satisfied. In order for a certain motion management option to be considered desirable, the criteria with the flag "Y" needs to be met. For example, referring to the first motion management option "gating or breath-hold at inhale" in the data structure 600d, in order for the apparatus 400 to recommend this motion management option, the two criteria with the flag "Y" (in the fourth row) need to be met. The same is true for the other motion management options. During use, the apparatus 400 determines whether the criteria listed in the data structure 600d are met. Then the apparatus 400 accesses the data structure 600d, and compare the satisfied criteria with those listed in the data structure 600d. The apparatus 400 may then output motion management data indicating which of the available motion management options are desirable based on the comparison.

FIG. 6E illustrates a data structure 600e that may be used with the system of FIG. 1E. The data structure 600e may also be used to implement the algorithm of FIG. 3E. As shown in FIG. 6E, the data structure 600e includes a plurality of criteria (in different columns) that correspond with the criteria described with reference to the algorithm 300e of FIG. 3E. The data structure 600e also includes a plurality of motion management options in different rows. In other embodiments, the criteria may be arranged in different rows, and the different motion management motions may be arranged in different columns. As shown in the example, the data structure 600e includes flags "Y" that represents a satisfaction of a certain criterion. For example, a "Y" under the criteria "Target motion>5 mm" indicates that such criterion is satisfied. In order for a certain motion management option to be considered desirable, the criteria with the flag "Y" needs to be met. For example, referring to the first motion management option "motion management based on implanted marker in combination with external marker" in the data structure 600e, in order for the apparatus 400 to recommend this motion management option, the two criteria with the flag "Y" (in the first row) need to be met. The same is true for the other motion management options. During use, the apparatus 400 determines whether the criteria listed in the data structure 600e are met. Then the apparatus 400 accesses the data structure 600e, and compare the satisfied criteria with those listed in the data structure 600e. The apparatus 400 may then output motion management data indicating which of the available motion management options are desirable based on the comparison.

Also, in some embodiments, the apparatus 400 may be configured to receive an input from a user indicating which position monitoring system is being considered by the user. For example, the user may provide an input indicating that position monitoring using internal fiducial (like that described in the system of FIG. 1A) is being considered. In response to such user input, the apparatus 400 may then access a corresponding one of the data structures 600a-600e that corresponds with the selected position monitoring system. In the above example, the apparatus 400 may access the data structure 600a because such data structure 600a maps different criteria with different motion management options that are based on internal fiducial.

In addition, in some embodiments, the apparatus 400 may be configured to automatically select one of the algorithms 300a-300e based on the user input indicating the type of system for position monitoring. For example, if the user enters an input indicating that internal fiducial be used for position monitoring (like that described with reference to the system of FIG. 1A), the apparatus 400 may then selects algorithm 300a for determining which motion management option(s) is desirable based on the selected position monitoring system.

Furthermore, in one or more embodiments described herein, the apparatus 400 may be configured to provide settings suggestions at various gantry angles based on the type of motion monitoring system selected, and the motion management option(s). By means of non-limiting examples, the settings suggestions may be beam shape, beam energy, beam-on duration, etc.

Also, in one or more embodiments, the apparatus 400 may be configured to determine dose distribution changes that correspond with respective settings suggestions.

As illustrated in the above embodiments, the apparatus 400 and the method 480 are advantageous because they allow one or more desirable motion management technique(s) to be identified automatically and quickly. The data structures 600a-600e described above are also advantageous because they allow a processing unit to efficiently determine motion management data with minimal processing resources, while considering types of patient position/motion monitoring technique, as well as various different criteria. Accordingly, the data structures 600a-600e may improve efficiency of a processing unit that is configured to generate motion management data based on various parameters. In addition, the apparatus 400 and the method 480 provide technical advantageous in a real physical world in that they allow a user to select a motion management scheme based on a set of predefined rules and parameters, and to create a treatment plan based on such selected motion management scheme. Without the benefit of the apparatus 400 and/or the method 480, a user performing treatment planning may not know which motion management scheme is desirable and/or undesirable. The user may arbitrarily pick a motion management scheme for treatment planning. If a wrong motion management scheme is selected, the treatment plan will not be optimized, and/or may not provide a desirable treatment result (e.g., the motion of the target may not be tracked, compensated, and/or addressed accurately).

In the above embodiments, the apparatus 400 and the method 480 have been described with reference to evaluating various parameters/criterion for determining whether one or more motion management options are desirable or not. In other embodiments, the apparatus 400 may be configured to consider (and the method 480 may include consideration of) other parameter(s) for determining whether a motion management option is desirable or not. For example, motion signal latency may be considered. In some cases, if the latency of a motion signal is above a certain threshold, then the apparatus 400 may determine that a certain motion management option is not desirable.

In the above embodiments, the treatment system has been described as delivering radiation. In some cases, the treatment system may be configured to provide a proton beam, or other particle beams, for treating the patient. The proton beam (or other particle beam) may be considered as a form of radiation. Thus, as used in this specification, the term "radiation" is not limited to x-ray type radiation, and may include other forms of energy deliveries that "radiate" from a source.

Specialized Processing System

Figure 7:
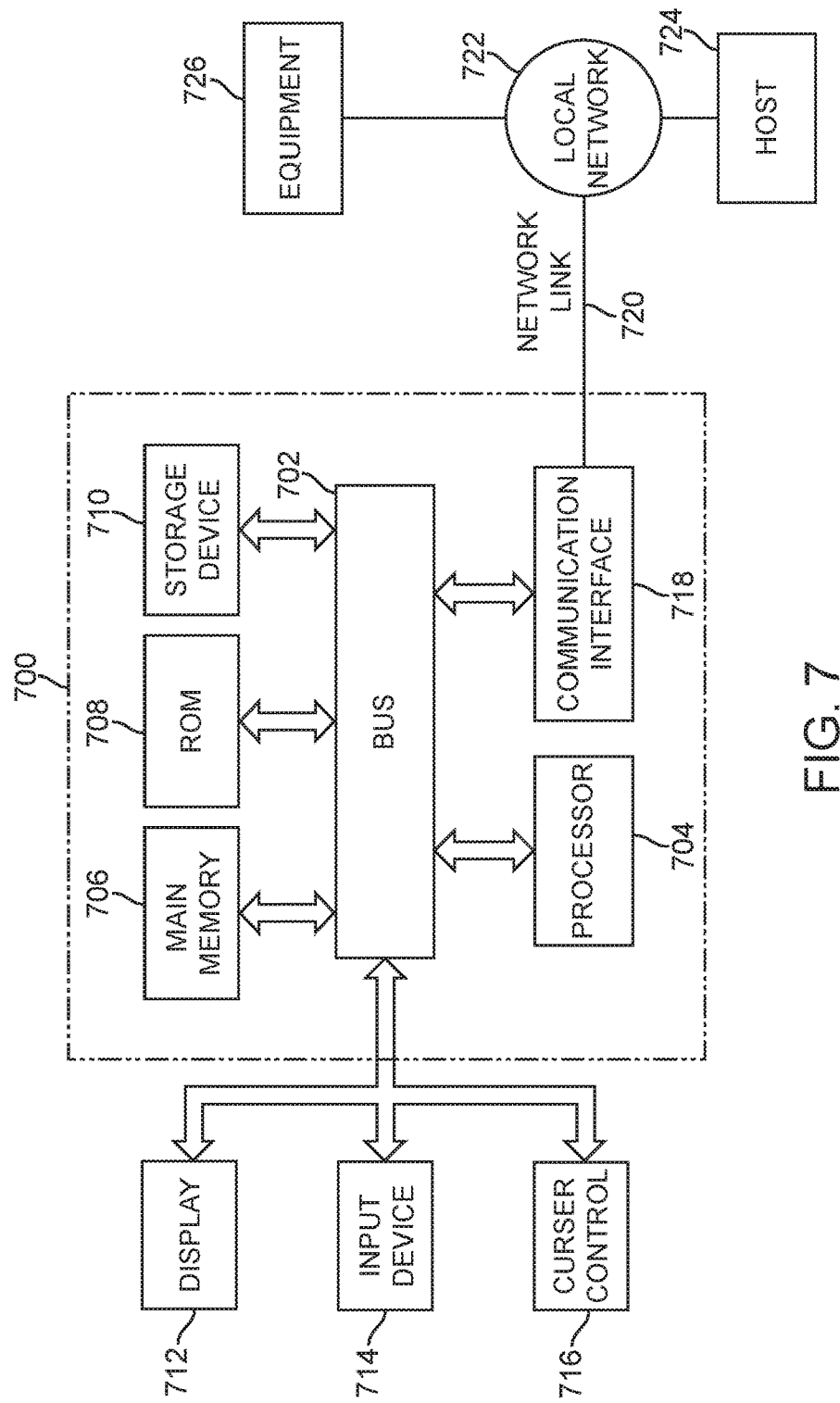
FIG. 7 is a block diagram of a specialized processing system.

FIG. 7 is a block diagram illustrating an embodiment of a specialized processing system 1600 that can be used to implement various embodiments described herein. For example, the processing system 1600 may be configured to perform the method 480 of FIG. 5. Also, in some embodiments, the processing system 1600 may be used to implement any of the algorithms 300a-300e. The processing system 1600 may also be an example of the apparatus 400. The processing system 1600 may also be any processor described herein. Also, in some embodiments, the processing system 1600 may be configured to use one, some, or all, of the data structures 600a-600e to determine whether one or more of a plurality of available motion management options are desirable, and to generate motion management data indicating the desirability and/or undesirability of one or more of the motion management options.

Referring to FIG. 7, the processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

The invention claimed is:

1. An apparatus for assisting a selection of motion management technique for use with a treatment machine having an energy source, the apparatus comprising:
one or more input for obtaining a motion trace of a target in a patient to be treated, and/or for obtaining motion data of a fiducial; and
a motion management processor configured to determine motion management data based at least in part on at least a portion of the motion trace of the target and/or at least a portion of the motion data of the fiducial, wherein the motion management data indicates desirability and/or undesirability of one or more motion management option(s);
wherein the motion management processor is also configured to output the motion management data for assisting the selection of the motion management technique for use with the treatment machine; and
wherein the apparatus comprises a synchronous motion detector, a visibility detector, a distance analyzer, or a combination of the foregoing, coupled upstream with respect to the motion management processor to provide information to the motion management processor.

2. The apparatus of claim 1, further comprising a target motion analyzer configured to determine whether a motion of the target is more than a prescribed amount.

3. The apparatus of claim 2, wherein the motion management data indicates that no motion management option is desirable if the motion of the target is less than the prescribed amount.

4. The apparatus of claim 1, wherein the fiducial comprises a surrogate inside the patient.

5. The apparatus of claim 4, further comprising a surrogate motion analyzer configured to determine whether a motion of the surrogate is more than a prescribed amount, wherein the motion management data indicates that motion management is desirable if the motion of the surrogate is less than the prescribed amount.

6. The apparatus of claim 1, wherein the fiducial comprises a surrogate inside the patient, and wherein the synchronous motion detector is configured to determine whether the surrogate moves synchronously with the target.

7. The apparatus of claim 6, wherein the motion management data indicates motion management based on surrogate is undesirable if the surrogate does not move synchronously with the target.

8. The apparatus of claim 1, wherein the fiducial comprises a marker coupled to the patient, and wherein the synchronous motion detector is configured to determine whether the marker moves synchronously with the target.

9. The apparatus of claim 8, wherein the motion management data indicates that motion management based on the marker is undesirable if the marker does not move synchronously with the target.

10. The apparatus of claim 1, wherein the fiducial comprises a marker, and wherein the visibility detector is configured to determine whether a motion of the marker is visible from an imaging direction; and
wherein the motion management processor is configured to determine whether the motion management data based at least in part on the motion of the marker is visible from the imaging direction.

11. The apparatus of claim 1, further comprising a target motion analyzer configured to determine whether the target stays at an inhale phase for more than a prescribed duration, wherein the motion management processor is configured to determine the motion management data based at least in part on whether the target stays at the inhale phase for more than the prescribed duration.

12. The apparatus of claim 11, wherein the motion management data indicates that gating-at-inhale and breath-hold-at-inhale are desirable motion management options if the target stays at the inhale phase for more than the prescribed duration.

13. The apparatus of claim 1, further comprising a target motion analyzer configured to determine whether the target stays at an exhale phase for more than a prescribed duration, wherein the motion management processor is configured to determine the motion management data based at least in part on whether the target stays at the exhale phase for more than the prescribed duration.

14. The apparatus of claim 13, wherein the motion management data indicates that gating-at-exhale and breath-hold-at-exhale are desirable motion management options if the target stays at the exhale phase for more than the prescribed duration.

15. The apparatus of claim 1, wherein the distance analyzer is configured to determine whether a distance between the target and a critical organ is more than a first threshold.

16. The apparatus of claim 15, wherein the motion management data indicates that field-tracking and/or couch-tracking is desirable motion management option(s) or not if the distance between the target and the critical organ is not more than the first threshold.

17. The apparatus of claim 15, wherein the distance analyzer is configured to determine whether the distance between the target and the critical organ is more than a second threshold that is larger than the first threshold.

18. The apparatus of claim 17, wherein the motion management data indicates that field-tracking or couch-tracking is a desirable motion management option if the distance between the target and the critical organ is not more than the second threshold.

19. The apparatus of claim 17, wherein the motion management data indicates that field-tracking in combination with couch-tracking is a desirable motion management option if the distance between the target and the critical organ is more than the second threshold.

20. The apparatus of claim 1, further comprising a display for displaying the motion management data.

21. The apparatus of claim 1, wherein the motion trace comprises a segmentation of the target.

22. The apparatus of claim 1, wherein the motion management processor is configured to provide the motion management data to a treatment planning module.

23. The apparatus of claim 1, wherein the one or more input is also configured to obtain a signal input representing a change of one or more parameters involved in a treatment planning; and
wherein the motion management processor is configured to perform calculation using the input to obtain new motion management data.

24. The apparatus of claim 1, wherein the motion trace of the target comprises a video formed by CT image data, MRI data, PET, ultrasound or x-ray image data.

25. The apparatus of claim 1, wherein the motion data represents a real motion or a simulated motion.

26. The apparatus of claim 1, wherein the motion trace, the motion data, or both, are data generated during a treatment session.

27. The apparatus of claim 1, wherein the motion management processor is configured to determine the motion management data based also on data generated during the treatment session.

28. The apparatus of claim 1, further comprising dosimetry analyzer configured to determine dosimetry impact of one or more of the motion management option(s).

29. The apparatus of claim 1, wherein the motion management processor is configured to analyze the motion trace and the motion data to determine whether a plurality of criteria is met;
wherein the motion management processor is configured to determine the motion management data based on a result of the analyzing.

30. The apparatus of claim 29, wherein the motion management processor is configured to classify a first subset of all available motion management options as desirable motion management option(s), and to classify a second subset of the available motion management options as undesirable motion management option(s) based on the result of the analyzing.

31. The apparatus of claim 1, wherein the motion management data also indicates one or more of: an amount of movement of the target over a breathing cycle, an amount of movement of the target inside a percentage of a breathing amplitude, an amount of movement of the target over a certain phase range of a breathing cycle, gantry angle(s) or a range of gantry angles at or over which a distance between the target and a critical structure is less than a prescribed value, a duration for which the target does not shift by more than a prescribed distance during an exhale phase, a duration for which the target does not shift by more than a prescribed distance during an inhale phase, motion information regarding an organ at risk, an amount of movement of a critical organ over a breathing cycle, an amount of movement of the critical organ inside a percentage of a breathing amplitude, an amount of movement of the critical organ over a certain phase range of the breathing cycle, a duration for which the critical organ does not shift by more than a prescribed distance during the exhale phase, a duration for which the critical organ does not shift by more than a prescribed distance during the inhale phase, dose volume parameter that depends on a chosen motion management scheme, an estimated treatment time, dose robustness measure based on motion variability, or any combination of the foregoing.

32. The apparatus of claim 1, wherein the motion management data comprises one or more setting recommendations selected from the group consisting of: gating window for performing gating of radiation deliveries, gating window at different gantry angles, a change in gating window(s) depending on angles or angle segments, tracking parameter(s) for MLC or couch, optimal collimator settings at different gantry positions, and parameter suggestion for predicting motion.

33. The apparatus of claim 1, wherein the motion management technique corresponds with one of the one or more motion management option(s).

34. A processor-implemented method for assisting a selection of motion management technique for use with a treatment machine having an energy source, comprising:
obtaining a motion trace of a target in a patient to be treated and/or motion data of a fiducial;
determining, using a motion management processor of an apparatus, motion management data based at least in part on at least a portion of the motion trace of the target and/or at least a portion of the motion data of the fiducial, wherein the motion management data indicates desirability and/or undesirability of one or more motion management option(s); and
outputting the motion management data for assisting the selection of the motion management technique for use with the treatment machine;
wherein the apparatus comprises a synchronous motion detector, a visibility detector, a distance analyzer, or a combination of the foregoing, coupled upstream with respect to the motion management processor to provide information to the motion management processor.

35. The method of claim 34, further comprising determining whether a motion of the target is more than a prescribed amount.

36. The method of claim 35, wherein the motion management data indicates that no motion management option is desirable if the motion of the target is less than the prescribed amount.

37. The method of claim 34, wherein the fiducial comprises a surrogate inside the patient.

38. The method of claim 37, further comprising determining whether a motion of the surrogate is more than a prescribed amount, wherein the motion management data indicates that motion management is desirable if the motion of the surrogate is less than the prescribed amount.

39. The method of claim 34, wherein the fiducial comprises a surrogate inside the patient, and the method further comprises determining, by the synchronous motion detector, whether the surrogate moves synchronously with the target.

40. The method of claim 39, wherein the motion management data indicates motion management based on surrogate is undesirable if the surrogate does not move synchronously with the target.

41. The method of claim 34, wherein the fiducial comprises a marker coupled to the patient, and the method further comprises determining, by the synchronous motion detector, whether the marker moves synchronously with the target.

42. The method of claim 41, wherein the motion management data indicates that motion management based on the marker is undesirable if the marker does not move synchronously with the target.

43. The method of claim 34, wherein the fiducial comprises a marker, and the method further comprises determining, by the visibility detector, whether a motion of the marker is visible from an imaging direction; and wherein the motion management data is determined based at least in part on whether the motion of the marker is visible from the imaging direction.

44. The method of claim 34, further comprising determining whether the target stays at an inhale phase for more than a prescribed duration, wherein the motion management data is determined based at least in part on whether the target stays at the inhale phase for more than the prescribed duration.

45. The method of claim 44, wherein the motion management data indicates that gating-at-inhale and breath-hold-at-inhale are desirable motion management options if the target stays at the inhale phase for more than the prescribed duration.

46. The method of claim 34, further comprising determining whether the target stays at an exhale phase for more than a prescribed duration, wherein the motion management data is determined based at least in part on whether the target stays at the exhale phase for more than the prescribed duration.

47. The method of claim 46, wherein the motion management data indicates that gating-at-exhale and breath-hold-at-exhale are desirable motion management options if the target stays at the exhale phase for more than the prescribed duration.

48. The method of claim 34, further comprising determining, by the distance analyzer, whether a distance between the target and a critical organ is more than a first threshold.

49. The method of claim 48, wherein the motion management data indicates that field-tracking and/or couch-tracking is desirable motion management option(s) or not if the distance between the target and the critical organ is not more than the first threshold.

50. The method of claim 48, further comprising determining, by the distance analyzer, whether the distance between the target and the critical organ is more than a second threshold that is larger than the first threshold.

51. The method of claim 50, wherein the motion management data indicates that field-tracking or couch-tracking is a desirable motion management option if the distance between the target and the critical organ is not more than the second threshold.

52. The method of claim 50, wherein the motion management data indicates that field-tracking in combination with couch-tracking is a desirable motion management option if the distance between the target and the critical organ is more than the second threshold.

53. The method of claim 34, further comprising displaying the motion management data.

54. The method of claim 34, wherein the motion trace comprises a segmentation of the target.

55. The method of claim 34, further comprising providing the motion management data, by a motion management module, to a treatment planning module.

56. The method of claim 34, further comprising:
obtaining input representing a change of one or more parameters involved in a treatment planning; and
performing calculation using the input to obtain new motion management data.

57. The method of claim 56, wherein the act of obtaining input and the act of performing calculation using the input are repeated.

58. The method of claim 34, wherein the motion trace comprises a video formed by CT image data, MRI data, PET, ultrasound or x-ray image data.

59. The method of claim 34, wherein the motion data represents a real motion or a simulated motion.

60. The method of claim 34, wherein the motion trace, the motion data, or both, are data generated during a treatment session.

61. The method of claim 34, further comprising obtaining data generated during a treatment session, wherein the motion management data is determined based also on the data generated during the treatment session.

62. The method of claim 34, further comprising determining dosimetry impact of one or more of the motion management option(s).

63. The method of claim 34, further comprising analyzing the motion trace and the motion data to determine whether a plurality of criteria is met;
wherein the motion management data is determined based on a result of the analyzing.

64. The method of claim 63, further comprising classifying a first subset of all available motion management options as desirable motion management option(s), and classifying a second subset of the available motion management options as undesirable motion management option(s) based on the result of the analyzing.

65. The method of claim 34, wherein the motion management data also indicates one or more of: an amount of movement of the target over a breathing cycle, an amount of movement of the target inside a percentage of a breathing amplitude, an amount of movement of the target over a certain phase range of a breathing cycle, gantry angle(s) or a range of gantry angles at or over which a distance between the target and a critical structure is less than a prescribed value, a duration for which the target does not shift by more than a prescribed distance during an exhale phase, a duration for which the target does not shift by more than a prescribed distance during an inhale phase, motion information regarding an organ at risk, an amount of movement of a critical organ over a breathing cycle, an amount of movement of the critical organ inside a percentage of a breathing amplitude, an amount of movement of the critical organ over a certain phase range of the breathing cycle, a duration for which the critical organ does not shift by more than a prescribed distance during the exhale phase, a duration for which the critical organ does not shift by more than a prescribed distance during the inhale phase, dose volume parameter that depends on a chosen motion management scheme, an estimated treatment time, dose robustness measure based on motion variability, or any combination of the foregoing.

66. The method of claim 34, wherein the motion management data comprises one or more setting recommendations selected from the group consisting of: gating window for performing gating of radiation deliveries, gating window at different gantry angles, a change in gating window(s) depending on angles or angle segments, tracking parameter(s) for MLC or couch, optimal collimator settings at different gantry positions, and parameter suggestion for predicting motion.

67. The method of claim 34, wherein the motion management technique corresponds with one of the one or more motion management option(s).

68. An apparatus for assisting a selection of motion management technique for use with a treatment machine having an energy source, the apparatus comprising:
one or more input for obtaining a motion trace of a target in a patient to be treated, and/or for obtaining motion data of a fiducial; and
a motion management processor configured to determine motion management data based at least in part on at least a portion of the motion trace of the target and/or at least a portion of the motion data of the fiducial, wherein the motion management data indicates desirability and/or undesirability of one or more motion management option(s);

wherein the motion management processor is also configured to output the motion management data for assisting the selection of the motion management technique for use with the treatment machine;

wherein the fiducial comprises a surrogate inside the patient or a marker coupled to the patient, and wherein the apparatus further comprises:

a distance analyzer configured to determine whether a distance between the target and a critical organ is more than a first threshold;

a target motion analyzer configured to determine whether a motion of the target is more than a prescribed amount, wherein the motion is due at least in part to a breathing of the patient, the breathing having an inhale phase and an exhale phase;

a surrogate motion analyzer configured to determine whether a motion of the fiducial is more than a prescribed amount;

a synchronous motion detector configured to determine if the fiducial moves synchronously with the target; and a visibility detector configured to determine whether the motion of the fiducial is visible from an imaging direction.

69. A processor-implemented method for assisting a selection of motion management technique for use with a treatment machine having an energy source, comprising:

obtaining a motion trace of a target in a patient to be treated and/or motion data of a fiducial;

determining, using a motion management processor, motion management data based at least in part on at least a portion of the motion trace of the target and/or at least a portion of the motion data of the fiducial, wherein the motion management data indicates desirability and/or undesirability of one or more motion management option(s); and outputting the motion management data for assisting the selection of the motion management technique for use with the treatment machine;

wherein the fiducial comprises a surrogate inside the patient or a marker coupled to the patient, and wherein the method further comprises:

determining, by a distance analyzer, whether a distance between the target and a critical organ is more than a first threshold;

determining, by a target motion analyzer, whether a motion of the target is more than a prescribed amount, wherein the motion is due at least in part to a breathing of the patient, the breathing having an inhale phase and an exhale phase;

determining, by a surrogate motion analyzer, whether a motion of the fiducial is more than a prescribed amount;

determining, by a synchronous motion detector, if the fiducial moves synchronously with the target; and determining, by a visibility detector, whether the motion of the fiducial is visible from an imaging direction.

\* \* \* \* \*